(12) United States Patent
Lasken et al.

(10) Patent No.: US 6,323,009 B1
(45) Date of Patent: Nov. 27, 2001

(54) MULTIPLY-PRIMED AMPLIFICATION OF NUCLEIC ACID SEQUENCES

(75) Inventors: Roger S. Lasken; Frank B. Dean, both of Guilford, CT (US); John Nelson, Neshanic Station, NJ (US)

(73) Assignee: Molecular Staging, Inc., New Haven, CT (US)

( * ) Notice: Subject to any disclaimer, the term of this patent is extended or adjusted under 35 U.S.C. 154(b) by 0 days.

(21) Appl. No.: 09/605,192

(22) Filed: Jun. 28, 2000

(51) Int. Cl.$^7$ ..................................................... C12P 19/34
(52) U.S. Cl. ................................. 435/91.1; 435/91.2
(58) Field of Search .................... 435/91.2; 536/24.33

(56) References Cited

U.S. PATENT DOCUMENTS

| | | |
|---|---|---|
| 4,965,188 | 10/1990 | Mullis et al. . |
| 5,001,050 | 3/1991 | Blanco et al. . |
| 5,198,543 | 3/1993 | Blanco et al. . |
| 5,409,818 | 4/1995 | Davey et al. . |
| 5,455,166 | 10/1995 | Walker . |
| 5,599,921 * | 2/1997 | Sorge et al. ............... 536/24.33 |
| 5,714,320 | 2/1998 | Kool . |
| 5,854,033 * | 12/1998 | Lizardi ........................... 435/91.2 |
| 5,871,921 | 2/1999 | Landegren et al. . |
| 5,876,924 | 3/1999 | Zhang et al. . |
| 5,942,391 | 8/1999 | Zhang et al. . |
| 6,077,668 | 6/2000 | Kool . |
| 6,096,880 | 8/2000 | Kool . |
| 6,124,120 * | 9/2000 | Lizardi ........................... 435/91.2 |

FOREIGN PATENT DOCUMENTS

WO 92/01813   2/1992   (WO) .

OTHER PUBLICATIONS

Skerra, A., Nucleic Acids Research, vol. 20, pp. 3551–3554 (1992).*

Ausubel, F.M. et al., Current Protocols in Molecular Biology, vol. 1, pp. 1.6.1–1.6.6, John Wiley & Sons, (1988).*

Nilsson, et al., "Padlock Probes: Circularizing Oligonucleotides for Localized DNA Detection," Science, vol. 265, pp. 2085–2088 (Sep. 20, 1994).

Lizardi, et al., "Mutation detection and single–molecular counting using isothermal rolling–circle amplification," Nature Genetics, vol;. 19, pp. 225–232 (Jul. 19, 1998).

Marshall, et al., "A biopolymer by any other name would bind as well: a comparison of the ligand–binding pockets of nucleic acids and proteins," Structure, pp. 729–734 (Jun. 15, 1997).

Blanco, et al., "Highly Efficient DNA Synthesis by the Phage Ø29 DNA Polymerase," The Journal of Biological Chemistry, Vo. 264, No. 15, pp. 8935–8940 (May 25, 1989).

* cited by examiner

Primary Examiner—Kenneth R. Horlick
Assistant Examiner—Teresa Strzelecka
(74) Attorney, Agent, or Firm—Elliot M. Olstein; Alan J. Grant

(57) ABSTRACT

Processes for the amplification of target DNA sequences in the form of single or double stranded circular DNA molecules, especially those present in colony and plaque extracts, using multiple specific and/or random sequence oligonucleotide primers are disclosed along with methods for detecting such amplified target sequences. A kit containing components for use in the invention is also described.

67 Claims, 9 Drawing Sheets

0.01 ng amplified M13 DNA

Signal G:225 T:88 A:112 C:52
DYEnamic™ ET Term. US80872

MULTIPLY-PRIMED AMPLIFICATION OF NUCLEIC ACID SEQUENCES

FIELD OF THE INVENTION

The present invention relates to processes for establishing multiple replication forks in rolling circle amplification so as to provide enhanced yields of amplification products, with quantitative advantages over previous rolling circle methods.

BACKGROUND OF THE INVENTION

A means of amplifying circular target DNA molecules is of value because such amplified DNA is frequently used in subsequent methods including DNA sequencing, cloning, mapping, genotyping, generation of probes, and diagnostic identification.

Heretofore, several useful methods were developed that permit amplification of nucleic acids. Most were designed around the amplification of selected DNA targets and/or probes, including the polymerase chain reaction (PCR), ligase chain reaction (LCR), self-sustained sequence replication (3SR), nucleic acid sequence based amplification (NASBA), strand displacement amplification (SDA), and amplification with Qβ replicase (Birkenmeyer and Mushahwar, *J. Virological Methods,* 35:117–126 (1991); Landegren, *Trends Genetics,* 9:199–202 (1993)).

In addition, several methods have been employed to amplify circular DNA molecules such as plasmids or DNA from bacteriophage such as M13. One has been propagation of these molecules in suitable host strains of *E. coli,* followed by isolation of the DNA by well-established protocols (Sambrook, J., Fritsch, E. F., and Maniatis, T. Molecular Cloning, A Laboratory Manual, 1989, Cold Spring Harbor Laboratory Press, Cold Spring Harbor, N.Y.). PCR has also been a frequently used method to amplify defined sequences in DNA targets such as plasmids and DNA from bacteriophage such as M13 (PCR Protocols, 1990, Ed. M. A. Innis, D. H. Gelfand, J. J. Sninsky, Academic Press, San Diego.) Some of these methods suffer from being laborious, expensive, time-consuming, inefficient, and lacking in sensitivity.

As an improvement on these methods, linear rolling circle amplification (LRCA) uses a primer annealed to a circular target DNA molecule and DNA polymerase is added. The amplification target circle (ATC) forms a template on which new DNA is made, thereby extending the primer sequence as a continuous sequence of repeated sequences complementary to the circle but generating only about several thousand copies per hour. An improvement on LRCA is the use of exponential RCA (ERCA), with additional primers that anneal to the replicated complementary sequences to provide new centers of amplification, thereby providing exponential kinetics and increased amplification. Exponential rolling circle amplification (ERCA) employs a cascade of strand displacement reactions, also referred to as HRCA (Lizardi, P. M. et al. *Nature Genetics,* 19, 225–231 (1998)). However, ERCA is limited to the use of just a single primer P1 annealed to the circular DNA target molecule, to the need to know the specific DNA sequence for the primer P1, and for the need of the circular DNA target molecule to be a single-stranded DNA circle.

The methods of the present invention (referred to herein as Multiply-Primed Rolling Circle Amplification—MPRCA) avoid such disadvantages by employing procedures that improve on the sensitivity of linear rolling circle amplification by using multiple primers for the amplification of individual target circles. The present invention has the advantage of generating multiple tandem-sequence DNA (TS-DNA) copies from each circular target DNA molecule. In addition, MPRCA has the advantages that in some embodiments the sequence of the circular target DNA molecule may be unknown while the circular target DNA molecule may be single-stranded (ssDNA) or double-stranded (dsDNA or duplex DNA). Another advantage of some embodiments of the present invention is that the amplification of single-stranded or double-stranded circular target DNA molecules may be carried out isothermally and/or at ambient temperatures. Other advantages include being highly useful in new applications of rolling circle amplification, low cost, sensitivity to low concentration of target circle, flexibility, especially in the use of detection reagents, and low risk of contamination.

In some embodiments of the present invention, procedures are employed that improve on the yield of amplified product DNA by using multiple primers that are resistant to degradation by exonuclease activity that may be present in the reaction. This has the advantage of permitting the primers to persist in reactions that contain an exonuclease activity and that may be carried out for long incubation periods. The persistence if primers allows new priming events to occur for the entire incubation time of the reaction, which is one of the hallmarks of ERCA and has the advantage of increasing the yield of amplified DNA.

The methods of the present invention allow for the first time "in vitro cloning", i.e. without the need for cloning into an organism, of known or unknown target DNAs enclosed in circles. A padlock probe may be used to copy the target sequence into a circle by the gap fill-in method (Lizardi, P. M. et al. *Nature Genetics,* 19,225–231 (1998)). Alternatively, target sequences can be copied or inserted into circular ssDNA or dsDNA by many other commonly used methods. The RCA amplification overcomes the need to generate amplified yields of the DNA by cloning in organisms.

One application envisioned is the targeted capture of known sequences from genomic or other complex DNAs. A second application is RCA of circles generated in a whole genome amplification method. Whole genome amplification involves randomly primed or specifically primed generation of a subset of genomic, cDNA or other complex DNA. Methods well known in the art can be used to circularize the products of whole genome amplification. Padlocks could also generate the circular targets. These circles would then constitute substrates for the targeted amplification of the present invention. Regardless of the means used to generate the circular products of whole genome amplification, the random priming RCA of the present invention would allow the selective amplification of the circles over the background of linear DNAs without the need for knowing sequences. Similarly, the circular DNA could contain known vector or target sequences that would allow use of specific primer sequences for multiple primer RCA.

The methods of the present invention are an improvement over LRCA in allowing increased rate of synthesis and yield. This results from the multiple primer sites for DNA polymerase extension. Random primer RCA also has the benefit of generating double stranded products. This is because the linear ssDNA products generated by copying of the circular template will themselves be converted to duplex form by random priming of DNA synthesis. Double stranded DNA product is advantageous in allowing for DNA sequencing of either strand and for restriction endonuclease digestion and other methods used in cloning, labeling, and detection.

It is also expected that strand-displacement DNA synthesis may occur during random priming RCA resulting in an exponential amplification. This is an improvement over conventional ERCA, also termed HRCA (Lizardi et al. (1998)) in allowing for the ability to exponentially amplify very large targets enclosed in circles. The amplification of large circular DNA, including bacterial artificial chromosomes (BACs), has been reduced to practice in the present invention. In practice, conventional ERCA has been limited to use of small circles of less than 200 nucleotides length.

Methods have published for whole genome amplification using degenerate primers (Cheung, V. G. and Nelson, S. F. *Proc. Natl. Acad. Sci. USA,* 93, 14676–14679 (1996) and random primers (Zhang, L. et al., *Proc. Natl. Acad. Sci. USA,* 89, 5847–5851 (1992) where a subset of a complex mixture of targets such as genomic DNA is amplified. Reduction of complexity is an objective of these methods. A further advantage of the method of the present invention is that, as an RCA reaction, it selectively amplifies circular DNA target molecules without the need for "subsetting", or reducing the complexity of the DNA target. Instead, the present invention takes advantage of the preferred amplification of circular target DNA over linear DNA molecules present in the same reaction.

BRIEF SUMMARY OF THE INVENTION

The present invention relates to a process for the enhanced amplification of circular DNA targets using either specific or random primers. It improves on the sensitivity of linear rolling circle amplification with singly-primed template circular DNA molecules. In a specific embodiment, this aspect of the invention employs multiple primers (specific or random, exonuclease-sensitive or exonuclease-resistant) annealed to the circular target DNA molecules to increase the yield of amplified product from RCA. Multiple primers anneal to multiple locations on the circle and a product of extension by polymerase is initiated from each location. In this way multiple extensions are achieved simultaneously from a single amplification target circle.

In separate embodiments of the foregoing methods, the use of multiple primers is achieved in several different ways. It is achieved by using two or more specific primers that anneal to different sequences on the circle, or by having one given primer anneal to a sequence repeated at two or more separate locations on the circle, or by using random or degenerate primers, which can anneal to many locations on the circle. Degenerate refers to an oligonucleotide in which one or more of the nucleotide positions is occupied by more than one base, i.e., a mixture of oligonucleotides of defined length in which one or more positions of an individual member of the mixture is occupied by a base selected at random from among more than one possibilities for that position. Such collections of oligonucleotides are readily synthesized using standard oligonucleotide synthesis instruments and software. Random refers to an oligonucleotide in which each of the nucleotide positions is occupied by a base selected at random from among a complete set of possibilities, but commonly limited to the four nucleosides, dAMP, dCMP, dGMP, or dTMP.

In some embodiments, the primers contain nucleotides, including all types of modified nucleotides, which may serve to make the primers resistant to enzyme degradation. Enzyme degradation may be caused by a pecific exonuclease such as the 3'-5' exonuclease activity associated with DNA polymerase or by a non-specific, contaminating exonuclease.

DETAILED SUMMARY OF THE INVENTION

Figure 1:
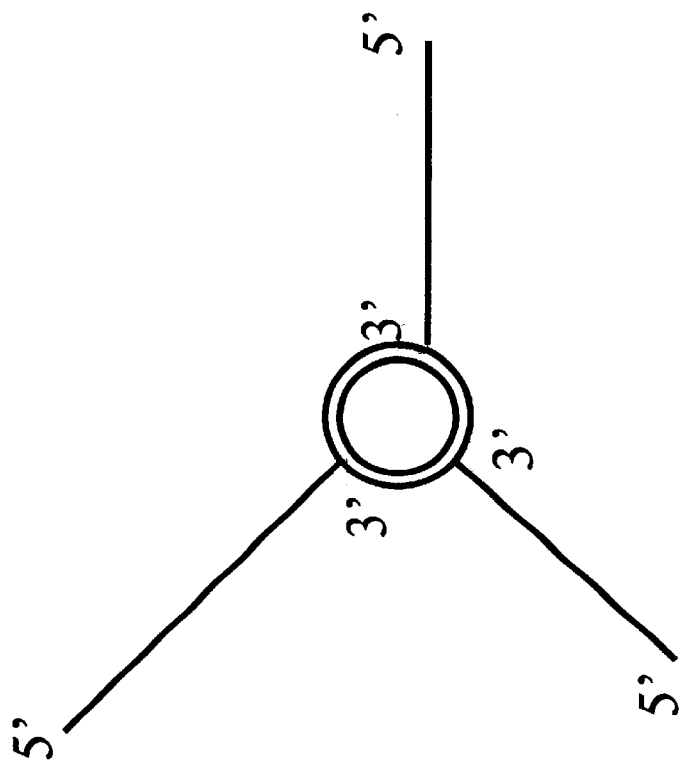
FIG. 1 shows a general embodiment of the methods according to the present invention wherein oligonucleotide primers with regions complementary to the amplification target circle (shown in A) hybridize specifically to the amplification target circle (shown in B). C shows the result of the addition of dNTPs, DNA polymerase, etc., to the hybridized structures of B, whereby the 3'-end of each primer is extended. Extension of each product continues, with the DNA polymerase displacing the DNA synthesized by the adjacent enzyme. In this case, one target circle interacts with 3 primers and 3 enzyme molecules to achieve 3 rounds of linear replication on the same amplification target circle template. More primers can be used. Multiple, specific primers may be used, or the primers may be of random sequence, hybridizing to the target circle at random locations.

The present invention relates to the use of multiple primers in nucleic acid sequence amplification using a circular DNA template as a means of greatly amplifying DNA synthesis and providing greatly increased signal amplification for detection of specific nucleic acid sequences contained in, for example, a target DNA where such target is in the form of a single stranded or double-stranded circular DNA or is part of such a circular DNA. While previous methods have often employed targets of substantial complexity, the present invention utilizes relatively simple targets, such as simple plasmid targets. The target DNA useful in the present invention also includes linear DNA, even high molecular weight linear DNA.

In addition, while other methodologies have attempted to amplify random subsets of substantially complex target DNA molecules (for example, a nucleic acid, including either DNA or RNA, whose presence in a sample is to be detected or whose sequence is to be amplified, such as for use in subsequent methods or procedures, or whose presence in said sample determines the identity of one or more other nucleic acids whose sequence(s) is/are to be amplified) to generate a less complex set of amplified materials, the present invention relates to the amplification of a single target, with no attempts at any reduction in complexity or other subsetting. It thereby takes advantage of the preferred amplification of a circular target over linear DNA molecules, for example, in DNA extracted from colonies or plaques.

In one aspect, the present invention relates to a process for selectively amplifying nucleic acid sequences, comprising forming a mixture comprising: multiple single stranded non-circular oligonucleotide primers (P1), one or more amplification target circles (ATCs), a DNA polymerase and multiple deoxynucleoside triphosphates, under conditions wherein said ATC binds to more than one of said multiple P1 primers and wherein conditions promote replication of said amplification target circle by extension of the P1 primers to form multiple tandem sequence DNA (TS-DNA) products.

Thus, in one embodiment one can provide a premix, such as in the form of a kit, comprising a polymerase, even including more than one polymerase, a protected oligonucleotide primer, such as a hexamer, the required nucleoside triphosphates, an appropriate buffer, a pyrophosphatase, and other potentially desirable components, either with each such component in a separate vial or mixed together in different combinations so as to form a total of one, two, three, or more separate vials and, for example, a blank or buffer vial for suspending an intended target nucleic acid for use in the amplification process. One embodiment of the present invention comprises a kit for amplifying DNA sequences comprising nuclease-resistant random primers, a DNA polymerase and one or more dexoyribonucleoside triphosphates (dNTPs), which dNTPs may of may be labeled, such as with a fluorescent moiety or with a radiolabel. In a separate embodiment, said DNA polymerase has 3'-5' exonuclease activity. In a preferred embodiment, said DNA polymerase is φ29 DNA polymerase.

In a specific application of such an embodiment, there is provided a process whereby a sample of nucleic acid, such as a DNA in the form of a circle, is suspended in a buffer, such as TE buffer, and then heated, cooled, and then contacted with the components recited above, either sequentially or by adding such components as the aforementioned premix with the conditions of temperature, pH and the like subsequently adjusted, for example by maintaining such combination at 30° C.

In addition, the conditions used in carrying out the processes disclosed according to the present invention may vary during any given application. Thus, by way of non-limiting example, the primers and ATCs may be added under conditions that promote hybridization and the DNA polymerase and nucleoside triphosphates added under different conditions that promote amplification without causing denaturation of the primer-ATC complexes that act as substrates for the polymerase or polymerases.

In another embodiment, the present invention relates to a process for selectively amplifying nucleic acid sequences, comprising:
(a) mixing multiple single stranded non-circular oligonucleotide primers (P1) and one or more amplification target circles (ATC) under conditions wherein said ATC forms a hybrid with more than one said multiple P1 primers to produce a primer-ATC sample mixture;
(b) adding a DNA polymerase and multiple deoxynucleoside triphosphates under conditions that promote replication of said amplification target circle by extension of the P1 primers to form multiple primary tandem sequence DNA (TS-DNA) products.

In carrying out the procedures of the present invention it is to be understood that there are numerous orders in which components can be added and the sequence of additions above are not intended to be limiting, but are to be read so as to include all order of addition combinations that one of ordinary skill in the art would recognize as being of interest or value in the particular context in which that discussion is presented. For example, all components could be added simultaneously in a one-step protocol or the DNA polymerase could be mixed with exonuclease-resistant primers prior to addition to DNA target.

In sum, the steps of said methods can be performed in any order in which they are recited herein but may be, where desired, advantageous, or otherwise convenient, performed in any suitable order so long as the objective and advantages of the invention are achieved. Thus, for example, the above recited process may be performed by mixing said primers and ATCs in a medium already containing said DNA polymerase.

In one embodiment, the present invention relates to a process as described herein wherein the ATC binds to, or hybridizes to, at least 3, 4, 5, even 10, or more primer oligonucleotides, each said primer producing, under appropriate conditions, a separate tandem sequence DNA molecule. Of course, because the sequences of the tandem sequence DNAs (TS-DNAs) are complementary to the sequences of the ATCs, which act as template, the TS-DNA products will all have the same sequence if the ATCs all have the same sequence, regardless of the sequence of the primers.

A sample embodiment of the present invention, using multiple (here, three) primers for each amplification target circle (ATC), is shown in FIG. 1. Oligonucleotide primers (each about 20–50 bases in length and shown in A) with regions complementary to separate segments of an amplification target circle hybridize specifically to the amplification target circle (shown in B). C shows the results of addition of dNTPs, DNA polymerase, etc., to the hybridized structures of B, whereby the 3'-end of each primer is extended. Extension of each product continues, with the DNA polymerase displacing the DNA synthesized by the adjacent enzyme. Oligonucleotide primers may optionally contain a region or sequence of nucleotides at the 5' end of said primers, which region or sequence of nucleotides is non-complementary to the ATC if such a non-complementary region or sequence of nucleotides is deemed useful for increasing the ability of the DNA polymerase to carry out strand-displacement DNA synthesis. In the specific embodiment shown here, one ATC interacts with 3 primers and 3 enzyme molecules to achieve 3 rounds of linear replication on the same amplification target circle template.

In separate embodiments, the oligonucleotide (P1) primers used in the methods of the invention may be either specific or random, with the latter being especially useful. As used herein, the term "specific" refers to a primer that has, or is engineered to have, a nucleotide sequence that is complementary, in the Watson-Crick sense, to a sequence present in the amplification target circle (ATC) and which serve to facilitate hybridization of the primer to the ATC, especially where said complementary sequence within the oligonucleotide primer includes the 3'-terminus of said primer. Such specific sequences may include, at their 5'-ends, a sequence not complementary to any portion of the ATC template, with the latter non-complementary portion serving to facilitate displacement of the TS-DNA during succeeding rounds of amplification. Where such specific primers are utilized, the number of primers binding to a given ATC will commonly be related to the number of corresponding complementary sites present on said ATC.

In a preferred embodiment, the primers used for amplification will have random sequences. As used herein, the term "random" means that said oligonucleotide primers (P1) have nucleotide sequences unrelated to the nucleotide sequences of the amplification target circle (ATC) that acts as template for amplification. The result of such a random relationship is that the locations on the ATC at which said random primers hybridize will also be random. In addition, because the primers have random sequences, instances will occur where a given primer may hybridize imperfectly to the ATC and have one or more of the nucleotides not complementary to the corresponding nucleotide(s) on the ATC. It is to be appreciated that such occurrences do not in any way serve to remove the use of such primers from the breadth of the present invention. For example, such occurrences will be unlikely to diminish the effectiveness of the random primers in initiating DNA synthesis on the ATC.

The oligonucleotide primers useful in the processes of the present invention can be of any desired length. For example, such primers may be of a length of from at least 2 to about 30 to 50 nucleotides long, preferably about 2 to about 35 nucleotides in length, most preferably about 5 to about 10 nucleotides in length, with hexamers and octamers being specifically preferred embodiments. Such multiple primers as are used herein may equally be specific only, or random only, or a mixture of both, with random primers being especially useful and convenient to form and use.

Although the embodiment depicted in FIG. 1 shows the use of specific primers (here, 3 in number but any number suffices), said primers can easily be random and can be of higher numbers. Thus, each primer bound to an ATC produces a replication fork as it is extended by the DNA polymerase around the ATC. The larger an ATC is, the more amplification forks that are expected to form. In accordance with the present invention, there are commonly amplification forks at about every 10 to about every 1000 nucleotides of the ATC template, with an amplification fork at about every 50 to about every 100 certainly being common, even at about every 10 or so nucleotides is not unexpected within the present invention.

The oligonucleotide primers of the present invention may have segments complementary to a portion of the ATC and the non-limiting example depicted in FIG. 1 merely shows the use of three such primers, all appearing to be of equal length. As already stated, however, the present invention is not limited in either the number of such primers binding to a given ATC, or in the length of such primers, or the sequences thereof, used in the same experiment may easily be of different lengths or may all be of the same length as shown in the figure.

Amplification target circles (ATCs) useful in the processes of the present invention are circular DNA or RNA molecules, either single or double stranded, including DNA-RNA hybrid molecules generally containing between 40 to 10,000 nucleotides. However, it is expected that there will be no upper limit to the size of the ATC. Where the ATC is a duplex circle, such numbers are intended to refer to base pairs rather than individual nucleotide residues. The ATCs useful in the processes disclosed herein may have functionally different portions, or segments, making them particularly useful for different purposes. At least two such portions will be complementary to one or more oligonucleotide primers and, when present, are referred to as a primer complementary portions or sites. Amplification target circles useful in the present invention include, for example, those derived directly from such sources as a bacterial colony, a bacteriophage, a virus plaque, a yeast colony, a baculovirus plaque, as well as transiently transfected eukaryotic cells. Such sources may or may not be lysed prior to obtaining the ATCs. Where such sources have been lysed, such lysis is commonly achieved by a number of means, including where the lysing agent is heat, an enzyme, the latter including, but not limited to, enzymes such as lysozyme, helicase, glucylase, and zymolyase, or such lysing agent may be an organic solvent.

Amplification target circles (ATCs) of the present invention comprise the target sequences to be amplified by the methods disclosed herein and in accordance with the present disclosure, the designation of P1 and ATC is meant to refer to an initial round of RCA and, by use of the appropriate sequences for the P1 primers, can easily be extended to use of additional such rounds of DNA amplification by addition of subsequent mixtures of oligonucleotide primers, designated P2 primers, having much the same properties as P1 primers but having segments complementary to one or more of the tandem sequence DNA products (which are themselves complementary to the starting ATCs). Of course, such further rounds of amplification are merely one option available for use with the processes of the invention and the design and execution of such additional rounds are well within the ordinary skill of those in the molecular biology arts and will not be further described herein.

In MPRCA, amplification occurs with each primer, thereby forming a concatemer of tandem repeats (i.e., a TS-DNA) of segments complementary to the primary ATC (or ATC) being replicated by each primer. Thus, where random primers are used, many such TS-DNAs are formed, one from each primer, to provide greatly increased amplification of the corresponding ATC sequence since the nucleotide sequence, or structure, of the product depends only on the sequence of the ATC used as template and not on the sequences of the oligonucleotide primers, whether the latter are random or specific or a mixture of both.

While previous technologies have utilized random primers [see, for example, Lizardi, U.S. Pat. No. 5,854,033], these have been used to amplify whole genomes or linear sequences and not the single stranded or duplex circles of the present invention.

The present invention provides an improvement over existing methods (Cheung, V. G. and Nelson, S. F. *Proc. Natl. Acad. Sci. USA,* 93, 14676–14679 (1996); Zhang, L. et al., *Proc. Natl. Acad. Sci. USA,* 89, 5847–5851 (1992)) by facilitating use of random or multiple primers in an amplification of linear DNA target with a DNA polymerase, such as φ29 DNA polymerase as a preferred enzyme for this reaction, along with exonuclease-resistant primers (as described below). Therefore, the present invention includes a method for the amplification of linear DNA targets, including high molecular weight DNAs, as well as genomic and cDNAs, that takes advantage of the characteristics of φ29 DNA polymerase and the exonuclease-resistant primers that are compatible with the 3'-5' exonuclease activity associated with φ29 DNA polymerase and wherein said linear DNA target may be used instead of an amplification target circle (ATC) or other circular DNA.

As already described, the amplification target circles utilized as templates for the amplification disclosed according to the present invention may be either single stranded DNA circles or duplex (double stranded) DNA circles. Where said ATCs are duplex, it may be desirable that at least one strand of said duplex contains a nick. Such nicks are commonly present in duplex circles but they may also be introduced into such circles, such as by enzymatic methods well known in the art, if not already present therein. Alternatively, the presence of a nick in one strand of a duplex circle may be neither desirable nor necessary. The two strands of a duplex DNA circle may be denatured or unwound sufficiently in the absence of any nicks by procedures known to those skilled in the art to allow the hybridization of multiple primers necessary for MPRCA.

Where duplex circles are employed, amplification will commonly occur from both strands as templates. Simultaneous amplification of both circles may or may not be desirable. In cases where the duplex circles are to be further employed in reactions designed to sequence the DNA of said circles, amplification of both strands is a desirable feature and so the duplex circles can be directly employed without further processing (except for formation of a nick if needed). However, for other uses, where co-temporal amplification of both strands is not a desired feature, it is well within the skill of those in the art to denature and separate the strands prior to amplification by the processes of the present invention or, alternatively, to employ multiple specific primers that contain sequences complementary to only one of the two strands of the duplex circular template. No doubt other useful strategies will immediately occur to those of skill in the art and need not be further described herein.

Depending upon the size of the amplified circle, whether it is single stranded or duplex in structure, and the DNA polymerase used, MPRCA achieves an extremely high degree of amplification (and sensitivity) that can be optimized for the numbers of circles (often determined ad hoc for the particular primers and target sequences to be employed), DNA polymerases, dNTPs and $Mg^{2+}$.

In some circumstances it may be desirable to quantitatively determine the extent of amplification occurring and/or the amount of TS-DNA being formed or, in some circumstances, to be able to measure in a discriminating fashion the relative quantities of amplification target circles being formed where the ATCs of the starting mixture are not uniform in structure and/or size. In such instances, the present invention works well with any number of standard detection schemes, such as where special deoxynucleoside triphosphates (dNTPs) are utilized that make it easier to do quantitative measurements. The most common example is where such nucleotide substrates are radiolabeled or have attached thereto some other type of label, such as a fluorescent label or the like. Again, the methods that can be employed in such circumstances are many and the techniques involved are standard and well known to those skilled in the art. Thus, such detection labels include any molecule that can be associated with amplified nucleic acid, directly or indirectly, and which results in a measurable, detectable signal, either directly or indirectly. Many such labels for incorporation into nucleic acids or coupling to nucleic acid probes are known to those of skill in the art. General examples include radioactive isotopes, fluorescent molecules, phosphorescent molecules, enzymes, antibodies, and ligands.

Examples of suitable fluorescent labels include CyDyes such as Cy2, Cy3, Cy3.5, Cy5, And Cy5.5, available from Amersham Pharmacia Biotech (U.S. Pat. No. 5,268,486). Further examples of suitable fluorescent labels include fluorescein, 5,6-carboxymethyl fluorescein, Texas red, nitrobenz-2-oxa-1,3-diazol-4-yl (NBD), coumarin, dansyl chloride, and rhodamine. Preferred fluorescent labels are fluorescein (5-carboxyfluorescein-N-hydroxysuccinimide ester) and rhodamine (5,6-tetramethyl rhodamine). These can be obtained from a variety of commercial sources, including Molecular Probes, Eugene, OR and Research Organics, Cleveland, Ohio.

Labeled nucleotides are a preferred form of detection label since they can be directly incorporated into the products of RCA during synthesis. Examples of detection labels that can be incorporated into amplified DNA include nucleotide analogs such as BrdUrd (Hoy and Schimke, *Mutation Research*, 290:217–230 (1993)), BrUTP (Wansick et al., *J. Cell Biology*, 122:283–293 (1993)) and nucleotides modified with biotin (Langer et al., *Proc. Natl. Acad. Sci. USA*, 78:6633 (1981)) or with suitable haptens such as digoxygenin (Kerkhof, *Anal. Biochem.*, 205:359–364 (1992)). Suitable fluorescence-labeled nucleotides are Fluorescein-isothiocyanate-dUTP, Cyanine-3-dUTP and Cyanine-5-dUTP (Yu et al., *Nucleic Acids Res.*, 22:3226–3232 (1994)). A preferred nucleotide analog detection label for DNA is BrdUrd (BUDR triphosphate, Sigma), and a preferred nucleotide analog detection label is Biotin-16-uridine-5'-triphosphate (Biotin-16-dUTP, Boehringher Mannheim). Radiolabels are especially useful for the amplification methods disclosed herein. Thus, such dNTPs may incorporate a readily detectable moiety, such as a fluorescent label as described herein.

The present invention provides a means to achieve signal amplification in a variety of methods. In this case, the goal is to amplify a signal that allows detection or characterization of a target. In methods including, but not limited to cases where a DNA is detected by annealing of a labeled probe or by incorporation of a labeled nucleotide, or by labeling DNA product after synthesis, for example, by covalent modifications or intercalation of detectable molecules, the present invention provides a way to amplify DNA product and thereby signal intensity.

The methods of the present invention provide greatly increased amplification due to multiple priming events being induced on circular DNA molecules that are targets for amplification. Thus, the rate and extent of amplification is not limited to that accomplished by a single DNA polymerase copying the DNA circle. Instead, multiple DNA polymerases are induced to copy each template circle simultaneously, each one initiating from one of the primers. It is this feature that provides a unique advantage of the present method.

In one embodiment of the methods of the present invention, completely random primers are used for the amplification process, a particularly desirable process because the sequence of the ATC providing the template may not be known. Thus, any single stranded or duplex DNA circles can be readily used, with or without extensive purification, according to the methods disclosed herein. Thus, a major advantage of the use of random primers is that circular DNA targets of known or unknown sequence may be preferentially and selectively amplified from among a complex mixture of DNA molecules containing mixtures of both linear and circular DNA molecules.

A specific embodiment is described in Example 1, wherein bacteriophage M13 DNA having nine different oligonucleotide primers annealed at nine different sites around the circle provides for greater amplification than M13 DNA having six or fewer primers. Furthermore, M13 DNA having six different primers provides for greater amplification than M13 DNA having three or fewer primers. Finally, M13 DNA having three primers provides for greater amplification than M13 having just one primer.

Another specific embodiment is described in Example 2, wherein M13 DNA having random oligonucleotide primers annealed around the circle provides for greater amplification than that seen with M13 having just one primer.

Another specific embodiment is described in Example 3, wherein crude colony extracts are the source of circular plasmid DNA targets, and crude plaque extracts are the source of circular bacteriophage M13 DNA targets. These circular targets are preferentially amplified more than the bacterial DNA that is present using the methods of the present invention.

Another specific embodiment is described in Example 5, wherein M13 DNA having exonuclease-resistant random primers annealed around the circle provides for greater amplification than that seen with M13 having exonuclease-sensitive random primers. This is consistent with the results presented in Example 4 where it is shown that random primers absent such special exonuclease-resistant nucleotides are often readily degraded, especially in the presence of higher levels of an enzyme having exonuclease activity.

Another specific embodiment is described in Example 6, wherein DNA sequencing using template DNA amplified from 0.01 ng of input M13 DNA resulted in a signal strength that was similar to the signal achieved from 200 ng of non-amplified DNA template.

Another specific embodiment is described in Example 7, wherein crude colony extracts are the source of circular BAC DNA targets, and these BAC targets are preferentially amplified more than the bacterial DNA that is present using the methods of the present invention.

Another specific embodiment is described in Example 8, wherein amplification of human genomic DNA using exonuclease-resistant random hexamer instead of unmodified random hexamer can improve yields at least 200 fold.

Exonuclease-resistant primers useful in the methods disclosed herein may include modified nucleotides to make them resistant to exonuclease digestion. For example, a primer may possess one, two, three or four phosphorothioate linkages between nucleotides at the 3' end of the primer.

Thus, in some embodiments, the present invention relates to processes wherein the primers contain at least one nucleotide that makes the primer resistant to degradation, commonly by an enzyme, especially by an exonuclease and most especially by 3'-5'-exonuclease activity. In such an embodiment, at least one nucleotide may be a phosphorothioate nucleotide or some modified nucleotide. Such nucleotide is commonly a 3'-terminal nucleotide but the processes of the present invention also relate to embodiments wherein such a nucleotide is located at other than the 3'-terminal position and wherein the 3'-terminal nucleotide of said primer can be removed by 3'-5'-exonuclease activity.

It may also be advantageous within the present invention to provide a means for attaching an ATC template to a solid support. To accomplish this, one need only attach a single oligonucleotide primer to a solid support for each of the ATCs to be amplified. Thus, in carrying out the processes of the present invention, a given ATC will be attached to multiple primers, only one of which needs itself to be tethered to some type of solid support. Often, it is advantageous that such a tethering primer be bipolar, thus having two 3'-ends whereby one such end serves to attach the primer to the support while the other can attach to the circle and provide a primer for amplification. None of the other multiple primers attached to the ATC need be themselves attached to any type of support. The bipolar tethering primer may be specific or random without drawback to the processes disclosed herein. Examples of such bipolar primers, and their preparation and use, are well known in the literature [see, for example, the disclosure of Lizardi et al (1998), supra].

In addition, the ATCs of the present invention can also be utilized in a form in which they are directly attached, by whatever means is convenient, to some type of solid support, although attachment using an oligonucleotide primer is especially convenient and straightforward.

Attachment of ATCs or oligonucleotide primers to such supports can be through means of some molecular species, such as some type of polymer, biological or otherwise, that serves to attach said primer or ATC to a solid support. Such solid-state substrates useful in the methods of the invention can include any solid material to which oligonucleotides can be coupled. This includes materials such as acrylamide, cellulose, nitrocellulose, glass, polystyrene, polyethylene vinyl acetate, polypropylene, polymethacrylate, polyethylene, polyethylene oxide, glass, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, and polyamino acids. Solid-state substrates can have any useful form including thin films or membranes, beads, bottles, dishes, fibers, woven fibers, shaped polymers, particles and microparticles. A preferred form for a solid-state substrate is a glass slide or a microtiter dish (for example, the standard 96-well dish). Preferred embodiments utilize glass or plastic as the support. For additional arrangements, see those described in U.S. Pat. No. 5,854,033.

Methods for immobilization of oligonucleotides to solid-state substrates are well established. Oligonucleotides, including address probes and detection probes, can be coupled to substrates using established coupling methods. For example, suitable attachment methods are described by Pease et al., *Proc. Natl. Acad. Sci. USA* 91(11):5022–5026 (1994). A preferred method of attaching oligonucleotides to solid-state substrates is described by Guo et al., *Nucleic Acids Res.* 22:5456–5465 (1994).

Oligonucleotide primers and ATCs useful in the present invention can be synthesized using established oligonucleotide synthesis methods. Methods of synthesizing oligonucleotides are well known in the art. Such methods can range from standard enzymatic digestion followed by nucleotide fragment isolation (see for example, Sambrook, et al., Molecular Cloning: A Laboratory Manual, Second Edition, Cold Spring Harbor, N.Y., (1989), Wu et al, *Methods in Gene Biotechnology* (CRC Press, New York, N.Y., 1997), and *Recombinant Gene Expression Protocols, in Methods in Molecular Biology*, Vol. 62, (Tuan, ed., Humana Press, Totowa, N.J., 1997), the disclosures of which are hereby incorporated by reference) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., Ann. Rev. Biochem. 53:323–356 (1984), (phosphotriester and phosphite-triester methods), and Narang et al., Methods EnzymoL, 65:610–620 (1980), (phosphotriester method). Protein nucleic acid molecules can be made using known methods such as those described by Nielsen et al., Bioconjug. Chem. 5:3–7 (1994).

Methods for the synthesis of primers containing exonuclease-resistant phosphorothioate diesters by chemical sulfurization are well-established. The solid phase synthesis of random primers employs one or several specifically placed internucleotide phosphorothioate diesters at the 3'-end. Phosphorothioate triesters can be introduced by oxidizing the intermediate phosphite triester obtained during phosphoramidite chemistry with 3H-1, 2-benzodithiol-3-one 1,1 dioxide[1,2] or Beaucage reagent to generate pentavalent phosphorous in which the phosphorothioate triester exists as a thione. The thione formed in this manner is stable to the subsequent oxidation steps necessary to generate internucleotidic phosphodiesters. (Iyer, R. P., Egan, W., Regan, J. B., and Beaucage, S. L. J. Am. Chem. Soc., 112: 1253 (1990), and Iyer, R. P., Philips, L. R., Egan, W., Regan, J. B., and Beaucage, S. L. J. Org. Chem., 55: 4693 (1990))

Many of the oligonucleotides described herein are designed to be complementary to certain portions of other oligonucleotides or nucleic acids such that hybrids can be formed between them. The stability of these hybrids can be calculated using known methods such as those described in Lesnick and Freier, Biochemistry 34:10807–10815 (1995), McGraw et al., Biotechniques 8:674–678 (1990), and Rychlik et al., Nucleic Acids Res. 18:6409–6412 (1990).

DNA polymerases useful in the rolling circle replication step of RCA must perform rolling circle replication of primed single-stranded circles (or each strand of a duplex substrate). Such polymerases are referred to herein as rolling circle DNA polymerases. For rolling circle replication, it is preferred that a DNA polymerase be capable of displacing the strand complementary to the template strand, termed strand displacement, and lack a 5' to 3' exonuclease activity. Strand displacement is necessary to result in synthesis of multiple tandem copies of the ATC. A 5' to 3' exonuclease activity, if present, might result in the destruction of the synthesized strand. It is also preferred that DNA polymerases for use in the disclosed method are highly processive. The suitability of a DNA polymerase for use in the disclosed method can be readily determined by assessing its ability to carry out rolling circle replication. Preferred rolling circle DNA polymerases, all of which have 3', 5'-exonuclease activity, are bacteriophage φ29 DNA polymerase (U.S. Pat. Nos. 5,198,543 and 5,001,050 to Blanco et al.), phage M2 DNA polymerase (Matsumoto et al., Gene 84:247 (1989)), phage PRD1 DNA polymerase (Jung et al., Proc. Natl. Aced. Sci. USA 84:8287 (1987), and Zhu and Ito, Biochim. Biophys. Acta. 1219:267–276 (1994)), VENT™ DNA polymerase (Kong et al., J. Biol. Chem. 268:1965–1975 (1993)), Klenow fragment of DNA polymerase I (Jacobsen et al., Eur. J. Biochem. 45:623–627 (1974)), T5 DNA polymerase (Chatterjee et al., Gene 97:13–19 (1991)), and T4 DNA polymerase holoenzyme (Kaboord and Benkovic, Curr. Biol. 5:149–157 (1995)). φ29 DNA polymerase is most preferred. Equally preferred polymerases include T7 native polymerase, Bacillus stearothermophilus (Bst) DNA polymerase, Thermoanaerobacter thermohydrosulfuricus (Tts) DNA polymerase (U.S. Pat. No. 5,744,312), and the DNA polymerases of Thermus aquaticus, Thermus flavus or Thermus thermophilus. Equally preferred are the φ29-type DNA polymerases, which are chosen from the DNA polymerases of phages: φ29, Cp-1, PRD1, φ15, φ21, PZE, PZA, Nf, M2Y, B103, SF5, GA-1, Cp-5, Cp-7, PR4, PR5, PR722, and L17. In a specific embodiment, the DNA polymerase is bacteriophage φ29 DNA polymerase wherein the multiple primers are resistant to exonuclease activity and the target DNA is linear DNA, especially high molecular weight and/or complex linear DNA, genomic DNA, cDNA.

Strand displacement during RCA, especially where duplex ATCs are utilized as templates, can be facilitated through the use of a strand displacement factor, such as a helicase. In general, any DNA polymerase that can perform rolling circle replication in the presence of a strand displacement factor is suitable for use in the processes of the present invention, even if the DNA polymerase does not perform rolling circle replication in the absence of such a factor. Strand displacement factors useful in RCA include BMRF1 polymerase accessory subunit (Tsurumi et al., J. Virology 67(12):7648–7653 (1993)), adenovirus DNA-binding protein (Zijderveld and van der Vliet, J. Virology 68(2): 1158–1164 (1994)), herpes simplex viral protein ICP8 (Boehmer and Lehman, J. Virology 67(2):711–715 (1993); Skaliter and Lehman, Proc. Natl, Acad. Sci. USA 91(22): 10665–10669 (1994)), single-stranded DNA binding proteins (SSB; Rigler and Romano, J. Biol. Chem. 270:8910–8919 (1995)), and calf thymus helicase (Siegel et al., J. BioL Chem. 267:13629–13635 (1992)).

The ability of a polymerase to carry out rolling circle replication can be determined by testing the polymerase in a rolling circle replication assay such as those described in Fire and Xu, Proc. Natl. Acad. Sci. USA 92:4641–4645 (1995) and in Lizardi (U.S. Pat. No. 5,854,033, e.g., Example 1 therein).

In separate and specific embodiments, the target DNA may be, for example, a single stranded bacteriophage DNA or double stranded DNA plasmid or other vector, which is amplified for the purpose of DNA sequencing, cloning or mapping, and/or detection. The examples below provide specific protocols but conditions can vary depending on the identity of the DNA circles to be amplified.

Thus, in carrying out the procedures of the present invention it is to be understood that reference to particular buffers, media, reagents, cells, culture conditions, pH and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

The present invention is further described, for illustrative and not limiting purposes, by way of the following non-limiting examples. In applying the disclosure of these examples, it should be kept clearly in mind that other and different embodiments of the methods disclosed according to the present invention will no doubt suggest themselves to those of skill in the relevant art.

EXAMPLE 1

Increased Yield in Rolling Circle Amplification Using Multiple Specific Primers It is herein demonstrated that the yield of amplified DNA in RCA is increased when multiple primers are annealed to the substrate DNA. In RCA the yield of amplified DNA may be limited by the number of replication forks that have been established on the circular DNA template. The establishment of multiple replication forks on a single-stranded, circular DNA proportionally increases the number of points at which amplification occurs. The use of multiple primers annealed to a circular template DNA results in the establishment of multiple replication forks by the DNA polymerase. This example demonstrates that DNA synthesis is increased when multiple primers are annealed to the substrate DNA.

Primed M13 DNA was prepared as follows. Nine oligonucleotides were obtained that anneal to distinct sites around the M13 single-stranded viral (+) strand DNA. Annealing reactions contained M13 DNA and either one of the oligonucleotides, three of the oligonucleotides, six of the oligonucleotides, or all nine of the oligonucleotides. Annealing was carried out in reactions (100 μl) containing 20 mM Tris-HCl, pH 7.5, 40 mM NaCl, 6.5 μg of M13 viral (+) strand DNA (equivalent to 2.75 pmoles of M13 circles), and 50 pmoles of each oligonucleotide added. Under these conditions the oligonucleotide:circle ratio for each primer was 18:1. Reactions were heated to 95° C. for 1 minute and cooled slowly to room temperature over 30 minutes. The structures of the nine oligonucleotides were as follows:

Primer 1
5' TCTGTT TAT AGG GCC TCT TCG CTA TTA CGC CAG 3' (SEQ ID NO:1)
Primer 2
5' TTT TTT TTT TTT TTT CAG GGT GGT TTT TCT TTT CAC CAG CGA GAC GGG CAA CAG CTG ATT GCC CTT CAC CGC CTG 3' (SEQ ID NO:2)
Primer 3
5'TTT TTT TTT TTT TTT ACC ACA CCC GCC GCG CTT AAT GCG CCG CTA CAG GGC GCG TAC TAT GGT TGC TTT GAC GAG 3'(SEQ ID NO:3)
Primer 4
5' TTT TTT TTT TTC CTC AAG AGA AGG ATT AGG ATT AGC GGG G 3' (SEQ ID NO:4)
Primer 5
5' TTT TTT TTT TAC AAA AGG GCG ACA TTC AAC CGA TTG AGG G 3' (SEQ ID NO:5)
Primer 6
5' TTT TTT TTT TCC TGA ACA AAG TCA GAG GGT AAT TGA GCG C 3' (SEQ ID NO:6)
Primer 7
5' TTT TTT TTT TAC AAC ATG TTC AGC TAA TGC AGA ACG CGC C 3' (SEQ ID NO:7)
Primer 8
5' TTT TTT TTT TCA TCG GGA GAA ACA ATA ACG GAT TCG CCT G 3' (SEQ ID NO:8)
Primer 9
5' TTT TTT TTT TAT GCG CGA ACT GAT AGC CCT AAA ACA TCG C 3' (SEQ ID NO:9)

Four RCA reactions were carried out in order to illustrate the increased yield of DNA synthesis by using multiple primers annealed to single-strand, circular DNA. Reactions (50 μl) contained 20 mM Tris-HCl, pH 7.5, 7 mM MgCl$_2$, and 30 mM NaCl, 200 μM deoxyribonucleoside triphosphates, α-[$^{32}$P] dCTP, specific activity 40 cpm/pmol total dNTP, 12 ng primed M13 viral (+) strand DNA and 26 units T7 Sequenase.

Figure 2:
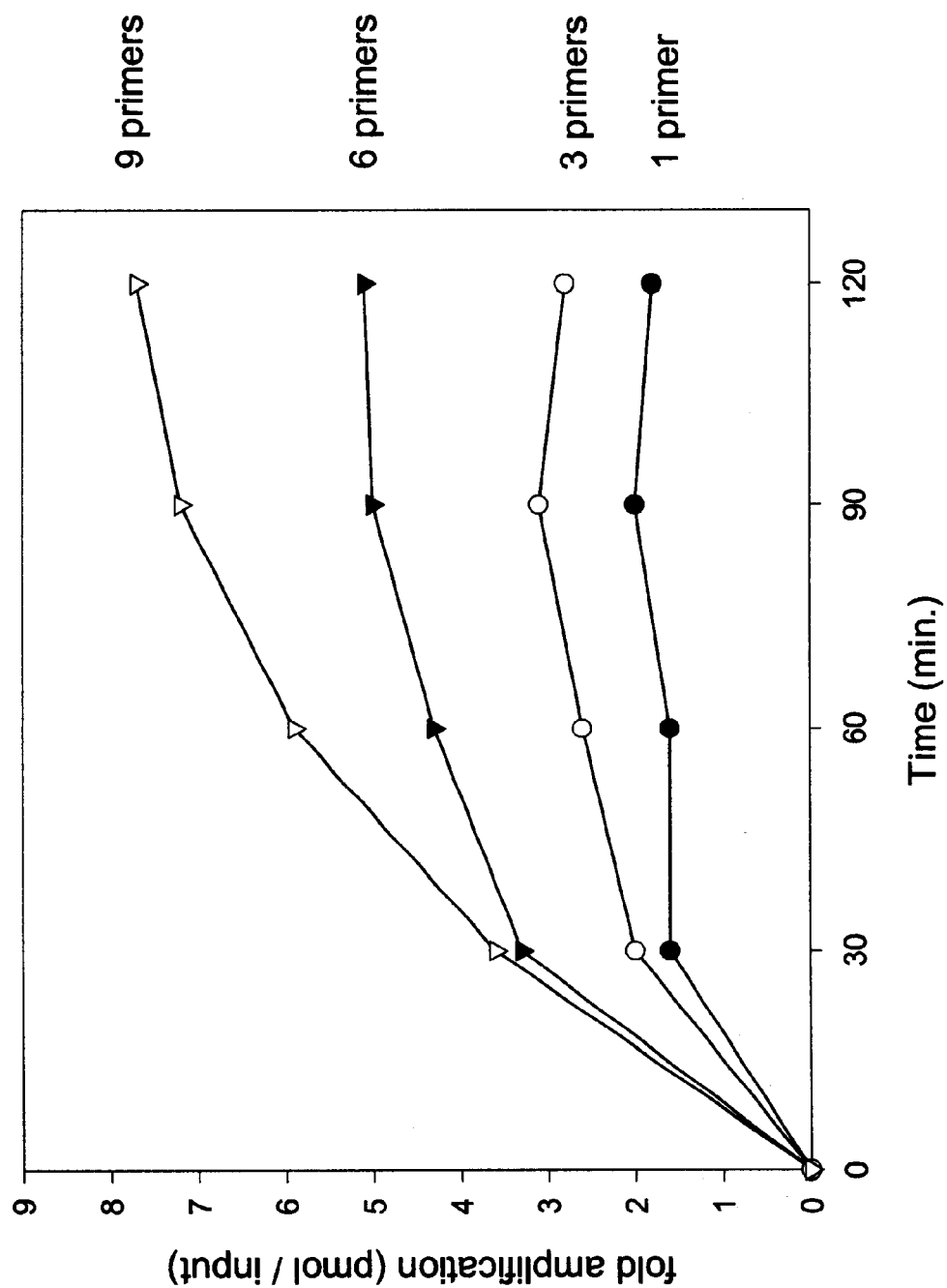
FIG. 2 is a graph of the fold amplification (in pmol/input or number of picomoles formed per pmol of starting template) amplification reactions using M13 with various numbers of annealed primers. The number of primers annealed to the M13 DNA substrate are indicated by annotations to the right of the graph next to the last data point in each curve. The plot using a single primer is a linear RCA (LRCA) reaction.

Reactions were incubated for 2 hours at 37° C. Aliquots were taken at 30, 60, 90, and 120 minutes and spotted onto a DE81 filter to quantitate DNA synthesis by the incorporation of radioactive deoxyribonucleotide. The fold amplification of the input M13 DNA was determined by dividing the pmol of deoxyribonucleotide incorporated by the pmol of deoxyribonucleotide present in the input M13 DNA. The results are shown in FIG. 2.

As can be seen, significantly more DNA synthesis occurs on M13 templates that have more primers annealed to them.

EXAMPLE 2

Increased Yield in Rolling Circle Amplification Using Random Hexamer Primers It was also demonstrated that the yield of amplified DNA in RCA is increased when multiple, random hexamer primers are annealed to the substrate DNA.

Primed M13 DNA was prepared as follows. Singly primed M13 was prepared as above. The annealing reaction for random-hexamer primed DNA contained M13 DNA and random hexamer oligonucleotides. The annealing was carried out in a reaction (60 μl) containing 20 mM Tris-HCl, pH 7.5, 20 mM KCl, 0.1 mM EDTA, 6 ng of M13 viral (+) strand DNA (equivalent to 2.5 fmoles of M13 circles), and 6000 pmoles of random hexamer primer. Under these conditions the primer:circle ratio was 2.4×10$^6$:1. Reactions were heated to 95° C. for 1 minute and cooled slowly to room temperature over 30 minutes.

Two RCA reactions were carried out in order to illustrate the increased yield of DNA synthesis by using random hexamer primers annealed to single-strand, circular DNA. Reactions (20 μl) contained 50 mM Tris-HCl, pH 7.5, 10 MM MgCl$_2$, 20 mM ammonium sulfate , and 200 μg/ml bovine serum albumin, 1 mM deoxyribonucleoside triphosphates, α-[$^{32}$P] dCTP, specific activity 24 cpm/pmol total dNTP, and 0.3 units ϕ29 DNA polymerase. The first reaction contained 1 ng of singly-primed M13 prepared as described in Example 1, while the second reaction contained 1 ng random hexamer-primed M13 prepared as described above.

Figure 3:
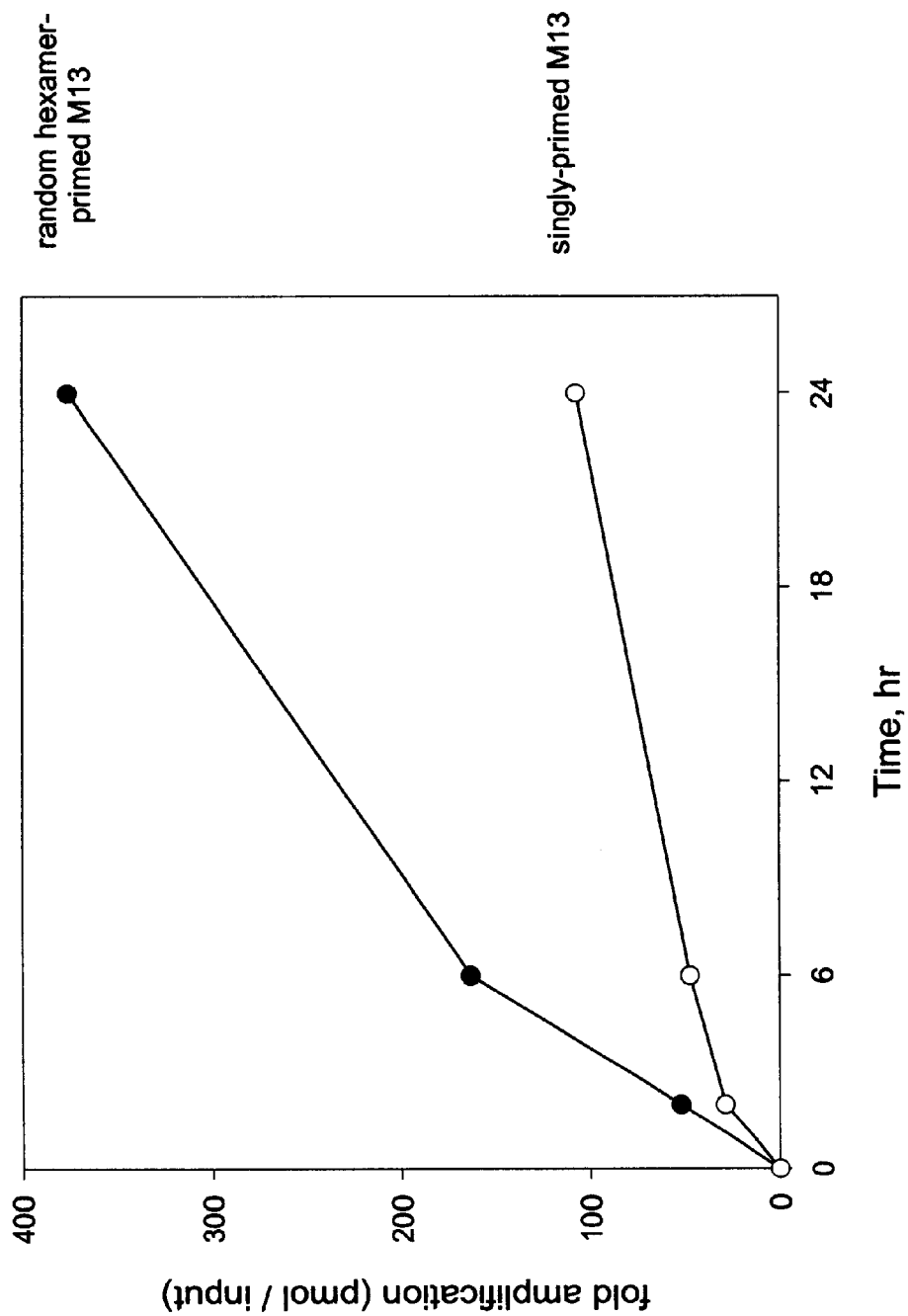
FIG. 3 is a graph of the fold amplification (in pmol/input; defined as the amount of DNA synthesis, as measured in pmoles of deoxynucleotide incorporated into product, divided by the amount of DNA template, as measured in pmoles of deoxynucleotide) versus time (in hours) during rolling circle amplification reactions using M13 with multiple random primers or just a single primer. The presence of random hexamer primers or just a single primer annealed to the M13 substrate are indicated by annotations to the right of the graph next to the last data point in each curve.

Reactions were incubated for 24 hours at 37° C. Aliquots were taken at 2, 6, and 24 hours and the incorporation of radioactive deoxyribonucleotide was determined. The fold amplification of the input M13 DNA was determined by dividing the pmol of deoxyribonucleotide incorporated by the pmol of deoxyribonucleotide present in the input M13 DNA. The results are shown in FIG. 3.

As can be seen, significantly more DNA synthesis occurs on M13 templates that have multiple random primers annealed to them (see random-hexamer-primed M13 curve), compared with M13 having a single primer (see singly-primed M13 curve). A 370-fold amplification of M13 DNA was achieved under these conditions, which has important utility for the amplification of small amounts of DNA template.

EXAMPLE 3

Rolling Circle Amplification of Plasmid and Bacteriophage DNA from Bacterial Colonies and Plaques Using Random Hexamer Primers It was also demonstrated that circular plasmid and bacteriophage DNA primed with multiple, random hexamer primers are specifically amplified from crude material taken from bacterial colonies or plaques using RCA.

DNA samples were prepared as follows. One end of a piece of polyethylene tubing (Intramedic, PE20, 1.09 mm outer diameter) 1 cm in length was stabbed into a colony of E. coli transformed with plasmid pUC19 or a plaque of bacteriophage M13 in a lawn of E. coli. For control reactions, the tubing was either not stabbed into a plate or else stabbed into a region of bacterial lawn containing no plaques nor bacteria transformed with plasmid. The tubing was then placed into a thermocycler tube (200 μl) containing 20 μl of buffer (20 mM Tris-HCl, pH 7.5, 40 mM NaCl, 1 mM EDTA). Random hexamer primer (1000 pmol) was added to each tube and the reactions were heated to 95° C. for 3 minutes and cooled slowly to room temperature over 30 minutes.

In order to carry out RCA the reactions were brought to a final volume of 40 μl containing final concentrations of 50 mM Tris-HCl, pH 7.5, 10 mM $MgCl_2$, 20 mM ammonium sulfate, 5% glycerol, 200 μg/ml of bovine serum albumin, 1 mM deoxyribonucleoside triphosphates, α-[$^{32}$P] dCTP, specific activity 67 cpm/pmol total dNTP, 0.04 units of yeast pyrophosphatase, and 0.6 units φ29 DNA polymerase.

Reactions were incubated for 8 hours at 37° C. After 8 hours an aliquot was taken and the incorporation of radioactive deoxyribonucleotide was determined. The amount of DNA synthesis was determined two ways. First, the amount of deoxynucleotide incorporated was used to calculate the number of nanograms of DNA synthesized. Second, the radioactively labeled reaction products were digested with restriction endonuclease EcoRI and the products were analyzed by electrophoresis through an agarose gel (1.0%, TBE). The linear products of amplification of M13 (7.2 kb) and pUC19 (2.7 kb) were quantitated and compared with known amounts of linear, radioactively labeled M13 DNA. The two measurements of the amount of amplified DNA yielded consistent results. The results are shown in Table 1.

Table 1 shows the yield of DNA (in ng) after plasmid and bacteriophage DNA primed with multiple, random hexamer primers were amplified from crude material taken from bacterial colonies or plaques. As can be seen, a significant yield of DNA is achieved from colonies (pUC19 plasmid DNA) or plaques (bacteriophage M13 DNA) compared with samples containing no plasmid or bacteriophage DNA.

TABLE 1

Quantitation of RCA yield from plaques and colonies

| # | Reaction | ng (from nucleotide) |
|---|---|---|
| 1 | no DNA | 0.4 |
| 2 | colony #1 | 25 |
| 3 | colony #2 | 16 |
| 4 | plaque #1 | 29 |
| 5 | plaque #2 | 25 |
| 6 | E. coli cells only | 2 |

Such methods provide substantial advantages over previous methods employed for sequencing genomic, cDNA or other complex DNAs:

1. Avoidance of the need for plasmid or phage minipreps that are slow, costly, labor intensive. Plasmid and phage growth are also limited by prevent "poisonous" sequences that are not tolerated by the bacterial host. This method potentially obviates each of these, and will reduce time required for growth and minipreps by about 24 hours.

2. Provision of a product that permits sequencing off both strands (in comparison with M13 phage minipreps that only permit sequencing off the phage strand).

3. Provision of a product that because of molecular size is ideally suited for exclusion upon electrokinetic injection employed by high-throughput capillary sequencers (manufactured by Amersham Pharmacia Biotech, Applied Biosystems, and Beckman Instruments for example). In contrast, phage or plasmid minipreps produce products that can cause blockage of capillaries if not present in the correct amount.

4. Provision of a DNA yields that are "normalized" between samples (plaques or colonies). That is, product amount can be configured to remain constant irrespective of input template amount, a feature that is highly advantageous in capillary sequencers where excess template addition will decrease the quality and read length of the sequence.

5. The method permits much greater flexibility in choice of vector for genomic sequencing. Subcloning may be decreased or eliminated. Currently BACs are subcloned into M13 phage or plasmids of very restricted composition. Partly or entirely synthetic subcloning vectors are made possible that can be designed to maximize genome coverage and minimize number of sequencing reactions.

EXAMPLE 4

Degradation of primers by the exonuclease activity of φ29 DNA polymerase

Random-hexamer primers were degraded in the presence of φ29 DNA polymerase under conditions used for RCA.

Primed M13 DNA was prepared as follows. Random-hexamer oligonucleotides were 5' end-labeled with $\gamma^{32}$P ATP to a specific activity of $1.3\times10^7$ cpm/pmol. Annealing reactions (60 μl) contained 20 mM Tris-HCl, pH 7.5, 40 mM NaCl, 1 mM EDTA, 6 ng of M13 viral (+) strand DNA (equivalent to 2.5 fmoles of M13 circles), and 6000 pmoles of labeled random hexamer primer. Under these conditions the primer:circle ratio was $2.4\times10^6$:1. Reactions were heated to 95° C. for 1 minute and cooled slowly to room temperature over 30 minutes.

In order to assess primer degradation by φ29 DNA polymerase under RCA conditions the reactions were brought to a final volume of 20 μl containing final concentrations of 50 mM Tris-HCl, pH 7.5, 10 mM $MgCl_2$, 20 mM ammonium sulfate, 5% glycerol, 200 μg/ml of bovine serum albumin, 1 mM deoxyribonucleoside triphosphates, 0.02 units of yeast pyrophosphatase, and 0.1, 1.0, and 10 units of φ29 DNA polymerase, as indicated.

Figure 4:
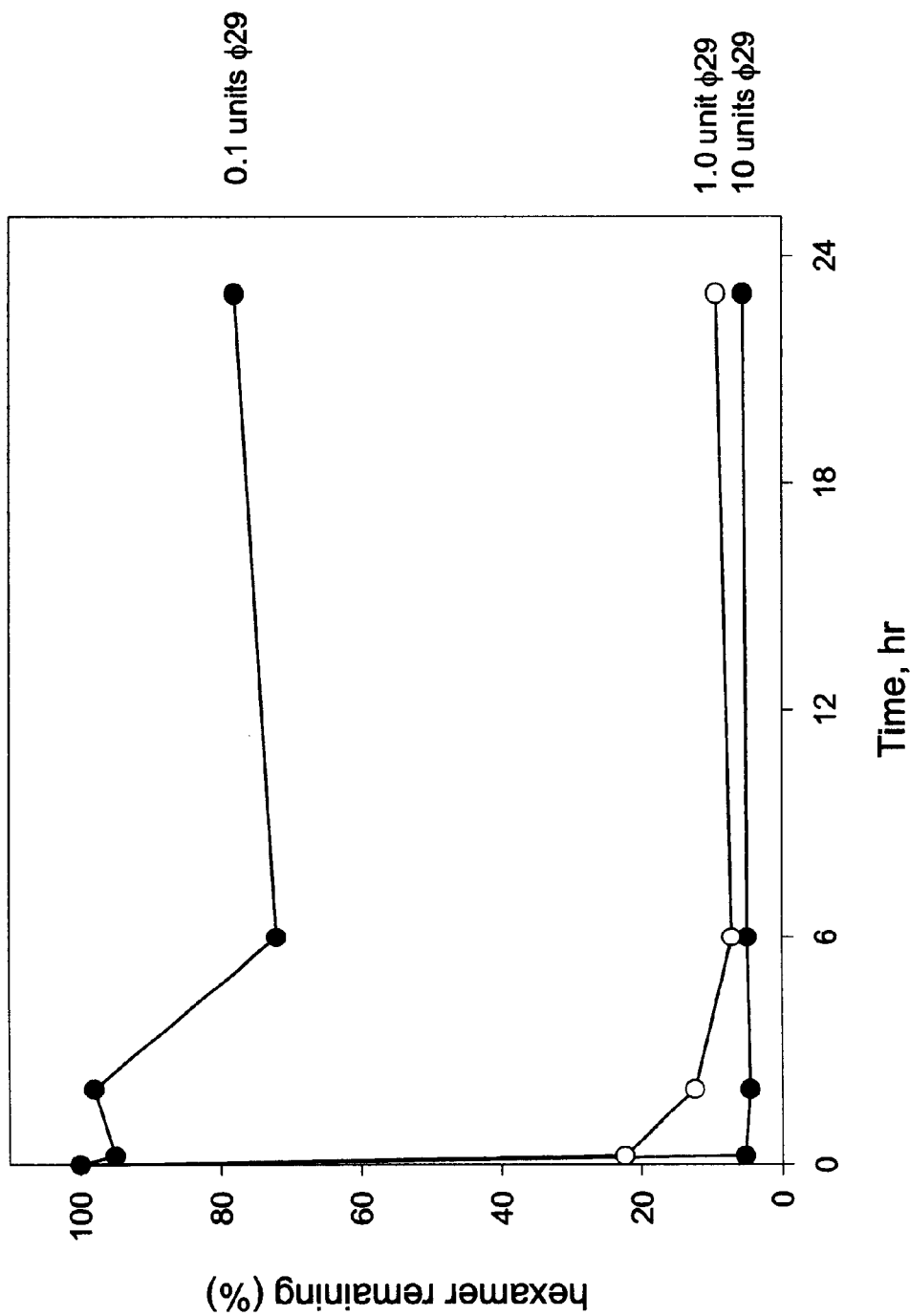
FIG. 4 is a graph of the extent of degradation of a primer, here a random hexamer, (in % primer remaining unreacted) versus time (in hours) by φ29 DNA polymerase. The amount of φ29 DNA polymerase present in each reaction is indicated by annotations to the right of the graph next to the last data point in each curve.

Reactions were incubated for 24 hours at 37° C. Aliquots (3μl) were taken at 0 time, 0.25, 2, 6, and 23 hr, and the reaction products were analyzed by electrophoresis through a 25% polyacrylamide sequencing gel. The results are shown in FIG. 4.

Random primers were completely degraded by 15 min in the presence of 10 units of φ29 DNA polymerase. Primers persisted for a longer time in the presence of 0.1 and 1.0 units of φ29 DNA polymerase.

Thus, the use of methods to prevent such degradation is advantageous. One such method is described in the following example.

EXAMPLE 5

Effect of exonuclease-resistant random primers on φ29 amplification of M13 RFI DNA It was demonstrated that circular, double-stranded bacteriophage DNA primed with multiple, exonuclease-resistant random hexamer primers is amplified to a greater extent than DNA primed with primers sensitive to exonuclease.

Exonuclease-resistant random hexamer primers were prepared by synthesizing a degenerate 7-mer oligonucleotide with the following structure, where N represents a random nucleotide and an underline represents a nucleotide with a 5'-thiophosphate linkage:

5' NNNN<u>NN</u>T 3'

In this 7-mer oligonucleotide the 3'-T residue is exonuclease-sensitive and the two penultimate 3'-random nucleotides are resistant to 3'->5'exonuclease activity. In the presence of a 3'->5' exonuclease the 3'-T residue is removed, yielding an exonuclease-resistant, random hexamer oligonucleotide.

Primed M13 DNA was prepared as follows. Annealing reactions (60 µl) contained 20 mM Tris-HCl, pH 7.5, 40 mM NaCl, 1 mM EDTA, 6 ng of M13 RFI DNA (equivalent to 2.5 fmoles of M13 circles), and 6000 pmoles of exonuclease-resistant random hexamer primer. Under these conditions the primer:circle ratio was $2.4 \times 10^6$:1. Reactions were heated to 95° C. for 1 minute and cooled slowly to room temperature over 30 minutes.

In order to carry out RCA the reactions were brought to a final volume of 20 µl containing final concentrations of 50 mM Tris-HCl, pH 7.5, 10 mM $MgCl_2$, 20 mM ammonium sulfate, 5% glycerol, 200 µg/ml of bovine serum albumin, 1 mM deoxyribonucleoside triphosphates, α-[$^{32}$p] dCTP, specific activity 67 cpm/pmol total dNTP, 0.02 units of yeast pyrophosphatase, and 0.3 units φ29 DNA polymerase.

Figure 5:
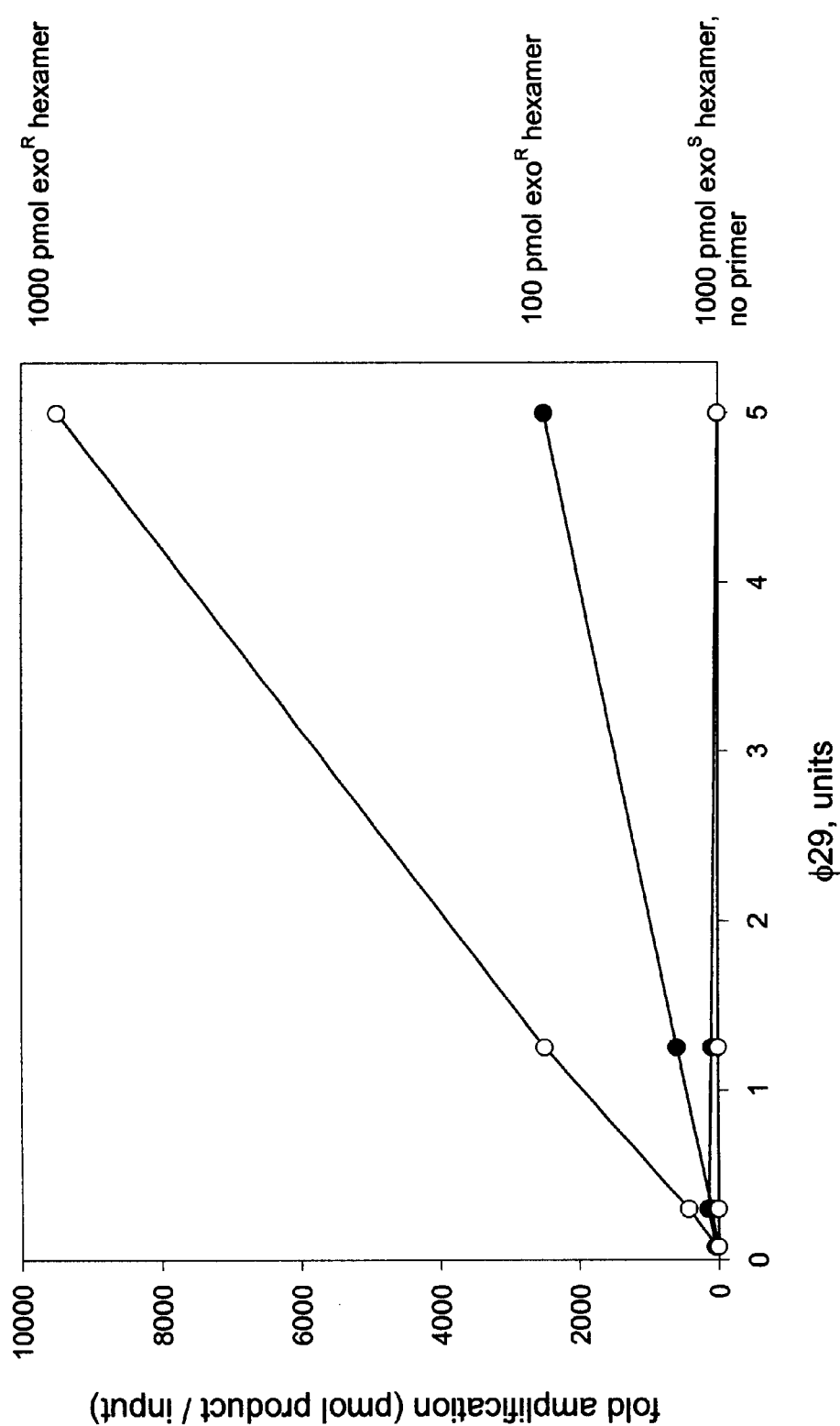
FIG. 5 is a graph of the fold amplification (in pmol product/input) versus amount of φ29 DNA polymerase added in the reaction (in units) during rolling circle amplification reactions using M13 with exonuclease-resistant (exo$^R$) or exonuclease-sensitive (exo$^S$) random primers. The presence of exo$^R$ or exo$^S$ random hexamer primers, or no primer, annealed to the M13 substrate are indicated by annotations to the right of the graph next to the last data point in each curve.
Figure 6A:
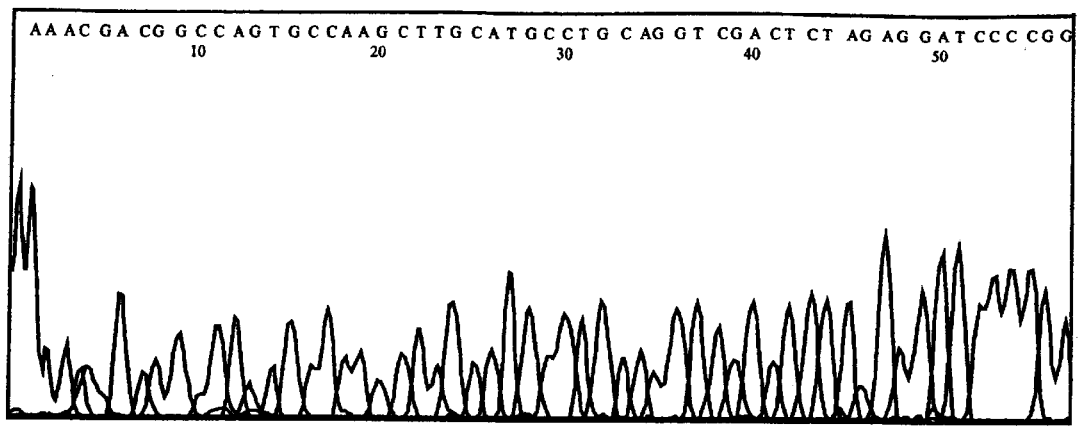
FIG. 6 is an electropherogram of a DNA sequencing reaction that depicts the result of carrying out a DNA sequencing reaction using DNA amplified by MPRCA from 0.01 ng of M13 DNA as the template. The nucleotide sequences follow over the panels of FIGS. 6A and 6B from top to bottom according to the residue numbers at the top of each panel.
Figure 6A:
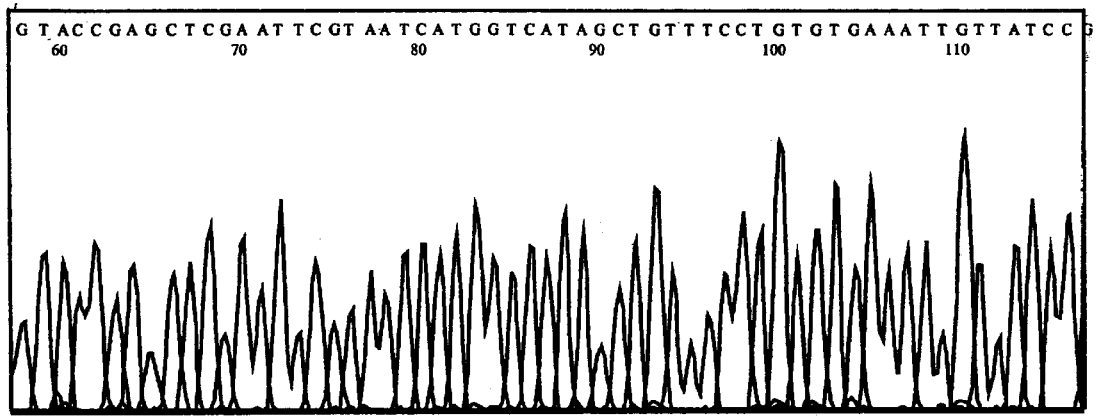
Figure 6A:
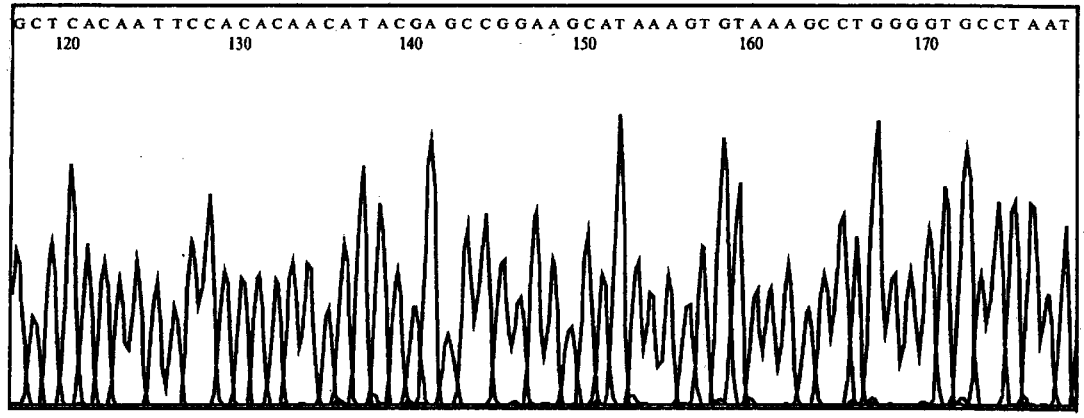
Figure 6B:
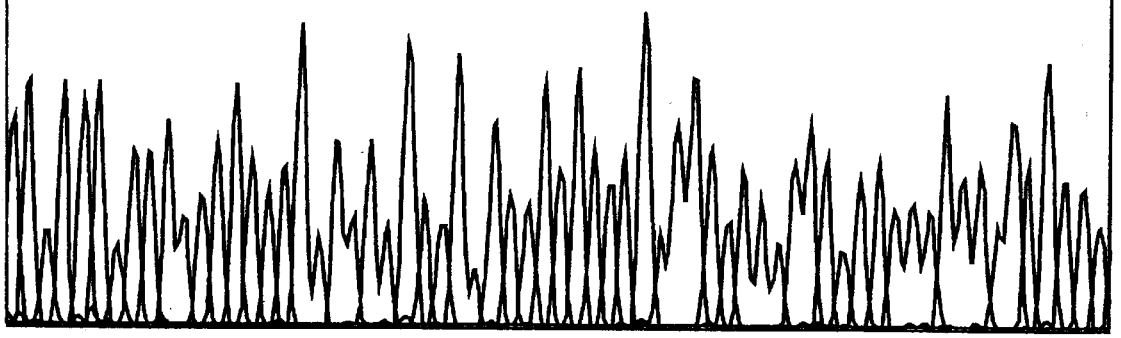
Figure 6B:
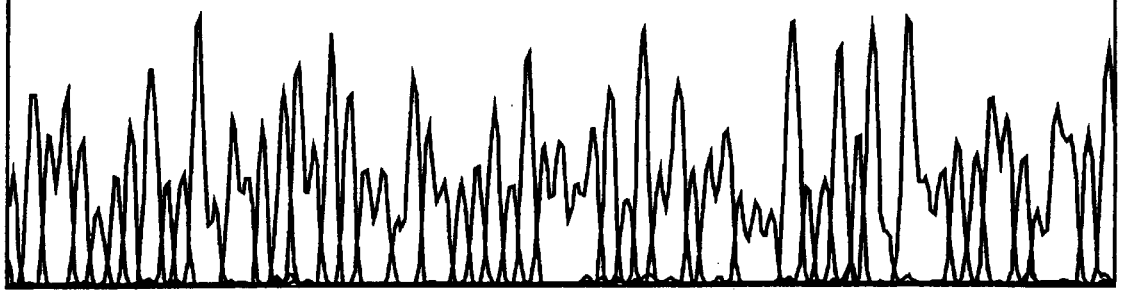
Figure 6B:
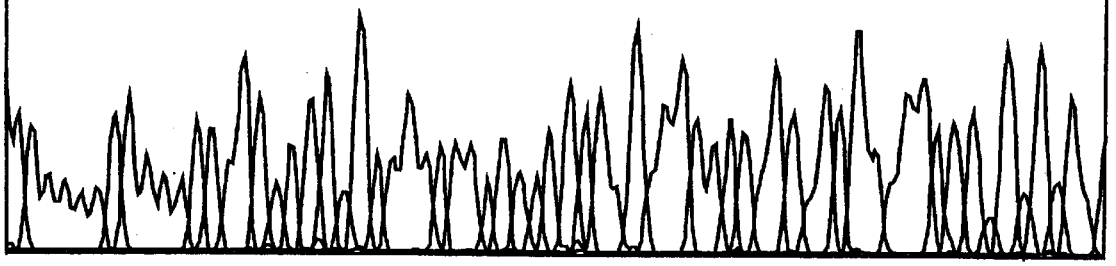
Figure 7A:
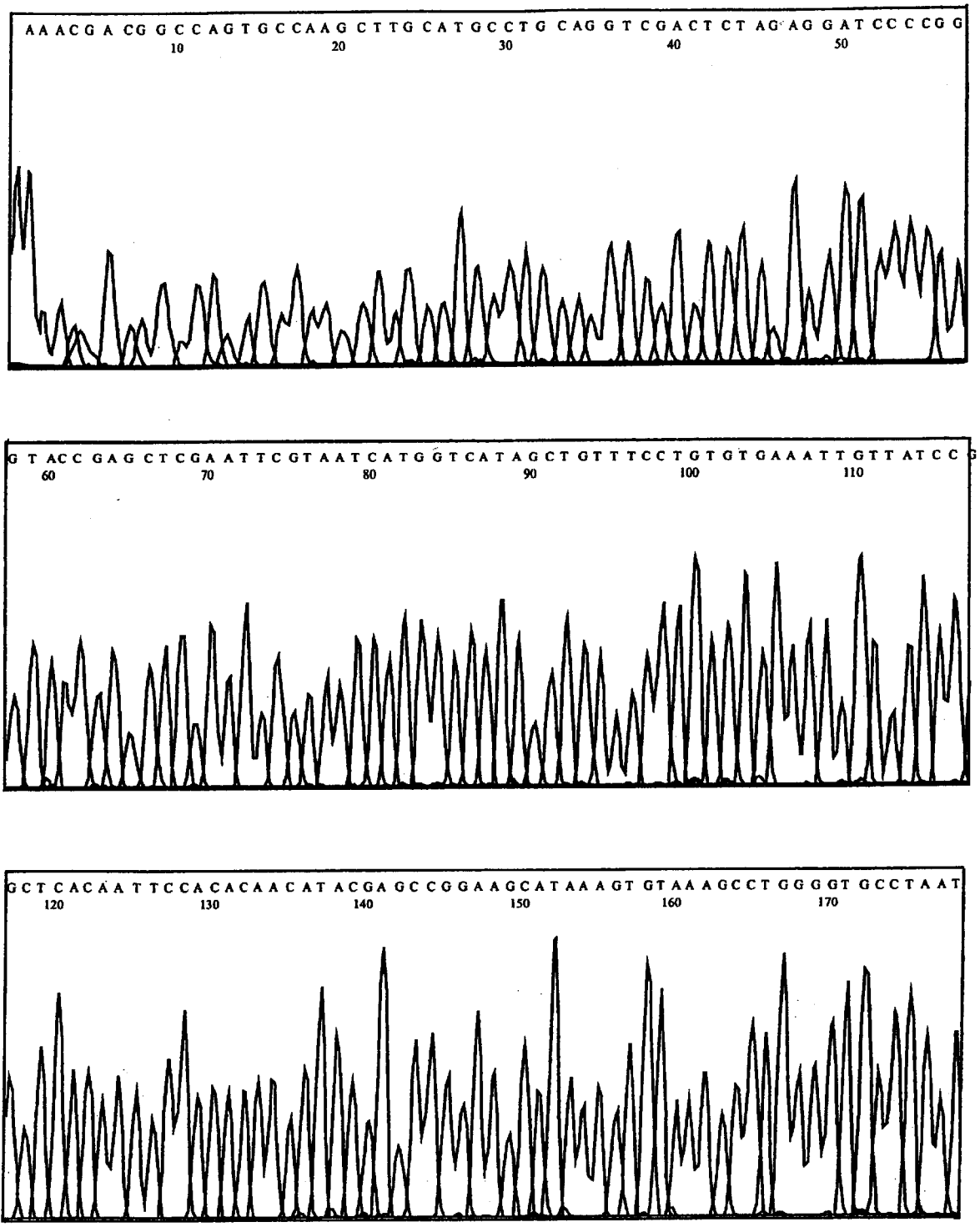
FIG. 7 is an electropherogram of a DNA sequencing reaction that depicts the result of carrying out a DNA sequencing reaction using 200 ng of M13 DNA as the template. The nucleotide sequences follow over the panels of FIGS. 7A and 7B from top to bottom according to the residue numbers at the top of each panel.
Figure 7B:
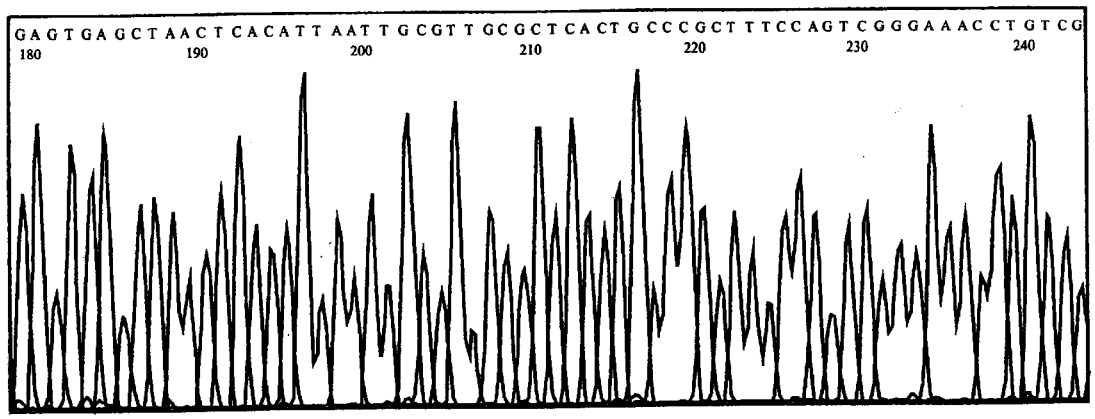
Figure 7B:
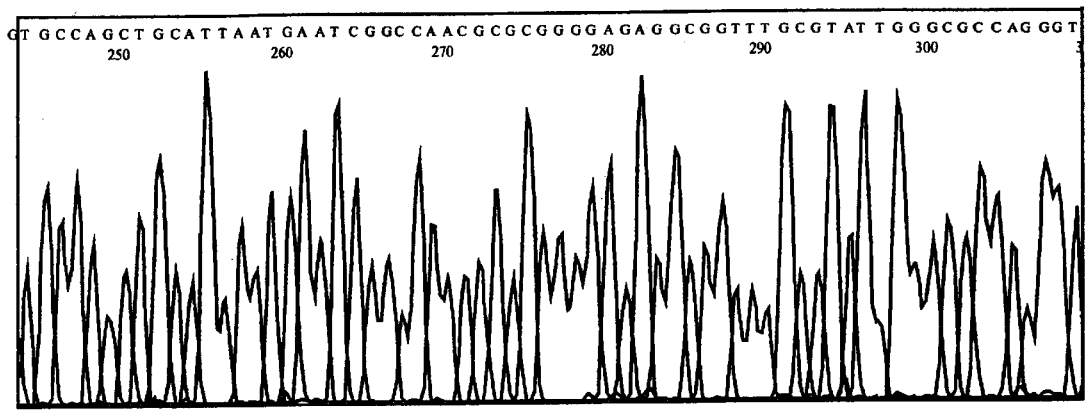
Figure 7B:
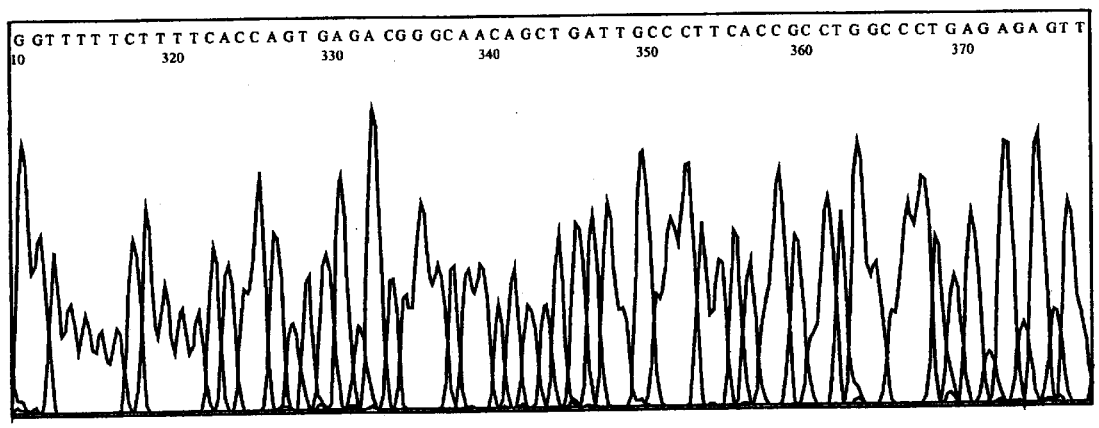

Reactions were incubated at 34° C. and after 13 hours an aliquot was taken and the incorporation of radioactive deoxyribonucleotide was determined. The fold amplification of the input M13 DNA was determined by dividing the pmol of deoxyribonucleotide incorporated by the pmol of deoxyribonucleotide present in the input M13 DNA. The results are shown in FIG. 5.

As can be seen, significant fold amplification of the input DNA occurs when the exonuclease-resistant ($exo^R$) primers are used. In addition, an increasing yield of fold amplification is seen as increasing amounts of φ29 DNA polymerase is added to the reactions (see 1000 pmol $exo^R$ hexamer and 100 pmol $exo^R$ hexamer curves). In contrast, the fold amplification using exonuclease-sensitive (exos) primers is much less than that seen with the $exo^R$ primers. In addition, optimal amplification using $exo^S$ primers is seen using 0.3 units of φ29 DNA polymerase, while higher levels of enzyme yielded less amplification (see 1000 pmol exos primer curve). No amplification was seen in the absence of added primer (see no primer curve). The use of exonuclease-resistant random primers allowed the achievement of over 9000-fold amplification using high concentrations of φ29 DNA polymerase, which has great utility for the amplification of very low levels of DNA template.

EXAMPLE 6

DNA Sequencing Using Template DNA Amplified by Rolling Circle Amplification Using Unmodified Random Hexamer Primers It was demonstrated that circular, single-stranded bacteriophage M13 DNA amplified using unmodified random hexamer primers is useful as a template for DNA sequencing.

Single-stranded M13mpl8 DNA (1 ng) was amplified in a 5 microliter reaction by combining with 62 pmoles of random hexamer, 2.5 units φ29 DNA polymerase, 0.007 units yeast inorganic pyrophosphatase in a buffer containing 25 mM Tris-HCl, pH 8.0, 10 mM $MgCl_2$, 75 mM KCl and 0.5 mM dNTP. The reaction was incubated at 30° C. for 12 hours to allow amplification of the M13 DNA. One unit of calf intestine alkaline phosphatase was added and the mixture was incubated at 37° C. for 30 minutes and then incubated at 95° C. for 3 minutes. To this reaction 495 microliters of water was added and 5 microliters of the diluted sample, containing the amount of DNA amplified from 0.01 ng of the input M13mp18 DNA, was transferred to a 20 microliter sequencing reaction containing 5 pmoles of −40 universal primer and 8 microliters of DYEnamic ET terminator premix (Amersham Pharmacia Biotech). This reaction was cycled through 95° C., 20 seconds and 60° C., 60 seconds, repeated 25 times, precipitated, and ½ of the product was applied to an ABI 373 sequencing gel apparatus. The resulting electropherogram is shown in FIG. 6. The sequence obtained was accurate over more than 400 nucleotides with an average signal strength of 119.

For comparison purposes, 200 ng of pure, non-amplified, single-stranded M13mpl8 DNA was used as a template for DNA sequencing exactly as described for amplified DNA. The resulting electropherogram is shown in FIG. 7. The sequence obtained was accurate to more than 400 nucleotides with an average signal strength of 425, about 3.6 times more than that obtained from DNA template amplified from 0.01 ng input DNA.

As can be seen, DNA sequencing using template DNA amplified from 0.01 ng of input M13 DNA resulted in a signal strength that was only about 4-fold weaker than the signal achieved from a 20,000-fold greater amount of non-amplified DNA template. Thus, DNA template amplification using the described methods has great utility in enabling the sequencing of small amounts of DNA template.

EXAMPLE 7

Rolling Circle Amplification of Bacterial Artificial Chromosome DNA from Bacterial Colonies Using Exonuclease-Resistant Random Hexamer Primers It was demonstrated that bacterial artificial chromosome (BAC) DNA primed with multiple, exonuclease-resistant random hexamer primers is specifically amplified from crude material taken from bacterial colonies using RCA.

DNA samples were prepared as follows. A BAC-containing bacterial strain (Research Genetics) was streaked out and grown up as single colonies. A piece of polyethylene tubing (Intramedic, PE20, 1.09 mm outer diameter) was stabbed into a colony and the tubing was placed into a thermocycler tube (200 µl) containing 10 µl of buffer (20 mM Tris-HCl, pH 8.0, 150 mM KCl, 0.1 mM EDTA). Exonuclease-resistant, random hexamer primer (random hexamer modified to contain two thiophosphate linkages located closest to the 3' end of the oligonucleotide, 350 pmol) was added to each tube and the reactions were heated to 95° C. for 3 minutes and cooled immediately to room temperature. In order to carry out RCA the reactions were brought to a final volume of 20 µl containing final concentrations of 25 mM Tris-HCl, pH 7.5, 10 mM $MgCl_2$, 75 mM KCl, 0.5 mM deoxyribonucleoside triphosphates, 0.03 units of yeast pyrophosphatase, and 2.0 units φ29 DNA polymerase.

Reactions were incubated for 4 hours at 30° C. After the reactions were terminated an aliquot was taken and DNA synthesis was quantitated photometrically using SYBR Green (Molecular Probes, Inc.) as recommended by the manufacturer. The amplified DNA was BAC DNA as determined by both restriction endonuclease analysis and DNA sequencing. The yield of amplified BAC DNA was 3 μg from a single bacterial colony. Thus, RCA using exonuclease-resistant random hexamer primers has great utility for the amplification BAC DNA directly from bacterial colonies.

EXAMPLE 8

Amplification of Human Genomic DNA Using Exonuclease-Resistant Random Hexamer Primers It was demonstrated that the amplification of human genomic DNA occurs to a greater extent using exonuclease-resistant random hexamer primers in comparison to human genomic DNA primed with exonuclease-sensitive primers.

Human genomic DNA (Promega) was amplified as follows. The DNA (20 ng) was mixed with 700 pmoles of either exonuclease-sensitive random hexamer or exonuclease-resistant random hexamer (i.e., random hexamer modified to contain 2 thiophosphate linkages located closest to the 3' end of the oligonucleotide) in a buffer consisting of 25 mM Tris HCl pH 8.0, 10 mM $MgCl_2$, 50 mM KCl, incubated at 95° C. for 3 minutes and cooled to 4° C. These mixtures were then combined with 64 units of ϕ29 DNA polymerase and 0.04 units of yeast inorganic pyrophosphatase in a buffer consisting of 25 mM Tris-HCl, pH 8.0, 10 mM $MgCl_2$, 50 mM KCl and 0.5 mM dNTP in a total volume of 50 microliters. The reactions were incubated at 30° C. for 16 hours to allow amplification of the DNA. Once amplified, the DNA product was quantitated photometrically using SYBR Green (Molecular Probes, Inc.) as recommended by the manufacturer. The DNA sample primed using random hexamer primer was amplified 2-fold while the DNA sample primed using the nuclease-resistant hexamer was amplified 400-fold. Thus, using exonuclease-resistant random hexamer instead of unmodified random hexamer can improve yields at least 200 fold and has great utility for the efficient amplification of high molecular weight DNA preparations such as human genomic DNA.

What is claimed is:

1. A process for selectively amplifying nucleic acid sequences, comprising forming a mixture comprising: multiple single stranded non-circular oligonucleotide primers (P1), one or more amplification target circles (ATCs), a DNA polymerase and multiple deoxynucleoside triphosphates, under conditions wherein said ATC binds to more than one of said multiple P1 primers and wherein conditions promote replication of said amplification target circle by extension of the P1 primers to form multiple tandem sequence DNA (TS-DNA) products wherein said ATC is derived directly from a culture and whereby said ATC is preferentially amplified over genomic DNA present in said culture.

2. The process of claim 1 wherein said multiple primers are primers with specific sequences complementary to portions of an ATC.

3. The process of claim 1 wherein said multiple primers are random primers.

4. The process of claim 1 wherein said multiple primers comprise a mixture of random and specific primers.

5. The process of claim 1 wherein said multiple primers are within the range of 2 to 50 nucleotides in length.

6. The process of claim 1 wherein said multiple primers are within the range of 2 to 35 nucleotides in length.

7. The process of claim 1 wherein said multiple primers are within the range of 2 to 10 nucleotides in length.

8. The process of claim 1 wherein said multiple primers are hexamers.

9. The process of claim 1 wherein said multiple primers are octamers.

10. The process of claim 1 wherein said multiple primers contain a region at the 5' end of said primers non-complementary to the ATC.

11. The process of claim 1 wherein said ATC is a single stranded DNA circle.

12. The process of claim 1 wherein said ATC is a duplex DNA circle having at least one nick.

13. The process of claim 1 wherein said ATC is a duplex DNA circle having no nicks.

14. The process of claim 1 wherein said ATC is a single stranded RNA circle.

15. The processes of claim 12 or claim 13 further comprising a denaturation step to separate the two strands of the duplex DNA circle.

16. The method of claim 15 where the amplification target circle is derived directly from a bacterial colony or virus plaque extract.

17. The method of claim 16 wherein said member has been lysed.

18. The method of claim 17 wherein lysis is achieved by treatment with an agent selected from the group consisting of heat, an enzyme, and an organic solvent.

19. The method of claim 18 where said enzyme is selected from the group consisting of lysozyme, helicase, glucylase, and xymolyase.

20. The process of claim 1 wherein said ATC is no larger than about 10,000 nucleotides in size.

21. The process of claim 1 wherein said ATC is larger than 10,000 nucleotides in size.

22. The process of claim 1 wherein said ATC is no larger than about 1,000 nucleotides in size.

23. The process of claim 1 wherein said ATC is no larger than about 100 nucleotides in size.

24. The method of claim 1 wherein the amplification target circle comprises a single stranded bacteriophage DNA, a double stranded DNA plasmid or other vector, or a clone derived from such a vector.

25. The method of claim 1 wherein the amplification target circle to be amplified is of unknown sequence composition.

26. The process of claim 1 wherein said dNTP is a member selected from the group consisting of dTTP, dCTP, dATP, dGTP, dUTP, a naturally occurring dNTP different from the foregoing, an analog of a dNTP, and a dNTP having a universal base.

27. The process of claim 26 wherein at least one said dNTP is radiolabeled.

28. The process of claim 26 wherein at least one nucleotide renders the TS-DNA resistant to nuclease activity following incorporation thereinto.

29. The process of claim 28 wherein said at least one nucleotide is a phosphorothioate nucleotide.

30. The process of claim 28 wherein said nuclease activity is due to an endonuclease.

31. The process of claim 28 wherein said nuclease activity is due to an exonuclease.

32. The process of claim 31 wherein said exonuclease activity is due to a polymerase having a 3'-5' exonuclease activity.

33. The process of claim 31 wherein said exonuclease activity is due to an added exonuclease enzyme.

34. The process of claim 28 wherein said nuclease activity is due to a contaminating nuclease.

35. The process of claim 28 wherein said at least one nucleotide is a modified nucleotide.

36. The process of claim 1 wherein at least one P1 primer is attached to a solid support.

37. The process of claim 36 wherein said solid support is made of glass or plastic.

38. The process of claim 1 wherein said multiple primers are selected from the group consisting of primers resistant to exonuclease activity, primers not resistant to exonuclease activity and a mixture of primers sensitive to exonuclease activity and resistant to exonuclease activity.

39. The process of claim 1 wherein said multiple primers are resistant to exonuclease activity and said target DNA is selected from the group consisting of linear DNA, genomic DNA and cDNA.

40. The process of claim 38 wherein said exonuclease activity is caused by an enzyme.

41. The process of claim 38 wherein said exonuclease activity is caused by a 3'-5'-exonuclease.

42. The process of claim 38 wherein said exonuclease activity is caused by a DNA polymerase having 3'-5'-exonuclease activity.

43. The process of claim 38 wherein said exonuclease activity is caused by a contaminating nuclease.

44. The process of claim 38 wherein each of said exonuclease-resistant primers contains at least one nucleotide making said primer resistant to exonuclease activity.

45. The process of claim 44 wherein said at least one nucleotide is a modified nucleotide.

46. The process of claim 45 wherein said modified nucleotide is a 3'-terminal nucleotide.

47. The process of claim 46 wherein said modified nucleotide is a phosphorothioate nucleotide.

48. The process of claim 44 wherein each of said exonuclease-resistant primers contains at least two nucleotides making said primer resistant to exonuclease activity.

49. The process of claim 35 wherein said at least one nucleotide is located at other than the 3'-terminal position.

50. The process of claim 35 wherein said 3'-terminal nucleotide of said primer can be removed by 3'-5'-exonuclease activity.

51. The process of claim 1 wherein said DNA polymerase is a DNA polymerase having 3', 5'-exonuclease activity and is a member selected from the group consisting of bacteriophage φ29 DNA polymerase, Tts DNA polymerase, phage M2 DNA polymerase, VENT™ DNA polymerase, Klenow fragment of DNA polymerase I, T5 DNA polymerase, PRD1 DNA polymerase, T4 DNA polymerase holoenzyme, T7 native polymerase and Bst DNA polymerase.

52. The process of claim 1 wherein said DNA polymerase is bacteriophage φ29 DNA polymerase.

53. The process of claim 1 wherein said DNA polymerase is bacteriophage (φ-29 DNA polymerase and said multiple primers are resistant to exonuclease activity.

54. The process of claim 1 wherein said DNA polymerase is bacteriophage φ29 DNA polymerase wherein said multiple primers are resistant to exonuclease activity and said target DNA is selected from the group consisting of linear DNA, genomic DNA and cDNA.

55. The process of claim 1 wherein said DNA polymerase does not exhibit 3', 5'-exonuclease activity.

56. The process of claim 55 wherein said DNA polymerase is selected from the group consisting of Taq, Tfl, and Tth DNA polymerase, Eukaryotic DNA polymerase alpha, and DNA polymerases that have been modified to eliminate 3'-5' exonuclease activity selected from the group consisting of the exo (−) versions of φ29 DNA polymerase, Klenow fragment, Vent and Pfu DNA polymerases.

57. The process of claim 1 wherein said DNA polymerase is a reverse transcriptase.

58. The process of claim 1 wherein said ATC is RNA and said DNA polymerase is a reverse transcriptase.

59. The process of claim 38 wherein said multiple primers are a mixture of primers sensitive to exonuclease activity and resistant to exonuclease activity.

60. The process of claim 38 wherein said DNA polymerase is φ29 DNA polymerase.

61. A process for selectively amplifying nucleic acid sequences, comprising:
  (a) mixing multiple single stranded non-circular oligonucleotide primers (P1) and one or more amplification target circles (ATC) under conditions wherein each said ATC binds to no more than one said multiple P1 primers to produce a primer-ATC sample mixture;
  (b) adding a DNA polymerase and multiple deoxynucleoside triphosphates under conditions that promote replication of said amplification target circle by extension of the P1 primers to form multiple primary tandem sequence DNA (TS-DNA) products and wherein the amplification target circle (ATC) is derived directly from a culture and whereby said ATC is preferentially amplified over genomic DNA present in said culture.

62. The method of claim 1 where at least one of the deoxyribonucleoside triphosphates comprises a readily detectable moiety.

63. The method of claim 62 where the detectable moiety is a fluorescent label.

64. The process of claim 1 wherein said culture is selected from the group consisting of bacterial colonies, virus plaques, yeast colonies, a baculovirus plaques, and transiently transfected eukarvotic cells.

65. The process of claim 1 wherein the amplification target circle (ATC) is selected from the group consisting of plasmid, virus, yeast artificial chromosomes (YAC), bacterial artificial chromosomes (BAC), and other nongenomic circular DNAs.

66. The process of claim 61 wherein said culture is selected from the group consisting of bacterial colonies, virus plaques, yeast colonies, a baculovirus plaques, and transiently transfected eukaryotic cells.

67. The process of claim 61 wherein the amplification target circle (ATC) is selected from the group consisting of plasmid, virus, yeast artificial chromosomes (YAC), bacterial artificial chromosomes (BAC), and other non-genomic circular DNAs.

* * * * *

UNITED STATES PATENT AND TRADEMARK OFFICE
CERTIFICATE OF CORRECTION

PATENT NO.   : 6,323,009 B1  
DATED        : November 27, 2001  
INVENTOR(S)  : Roger S. Lasken, Frank B. Dean and John Nelson It is certified that error appears in the above-identified patent and that said Letters Patent is hereby corrected as shown below:

Column 3,  
Line 64, delete "pecific" and insert therefor -- specific --

Column 6,  
Line 24, delete "addition" and insert therefor -- additional --

Column 16,  
Line 34, delete "MM" and insert therefor -- mM --  
Line 34, delete "sulfate ," and insert therefor -- sulfate, --

Column 19,  
Lines 43 and 47, delete "exos" and insert therefor -- $exo^s$ --

Column 20,  
Line 14, delete "1/2of" and insert therefor -- 1/2 of --

Signed and Sealed this

Twenty-eighth Day of January, 2003

JAMES E. ROGAN  
*Director of the United States Patent and Trademark Office*

SEQUENCE LISTING

<160> NUMBER OF SEQ ID NOS: 9

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence:
      Oligonucleotide primer that anneals to M13 (+)-strand DNA.

<400> SEQUENCE: 1
tctgtttata gggcctcttc gctattacgc cag                           33

<210> SEQ ID NO 2
<211> LENGTH: 75
<212> TYPE: DNA
<213> ORGANISM: Artificial Sequence
<220> FEATURE:
<223> OTHER INFORMATION: Description of Artificial Sequence:
      Oligonucleotide primer that anneals to M13 (+)-strand DNA.

<400> SEQUENCE: 2
tttttttttt tttttcaggg tggtttttct tttcaccagc gagacgggca acagctgatt     60
gcccttcacc gcctg                                                      75

<210> SEQ ID NO 3
<211> LENGTH: 75
<212> TYPE: DNA
<213> ORGANISM: Artificial Sequence
<220> FEATURE:
<223> OTHER INFORMATION: Description of Artificial Sequence:
      Oligonucleotide primer that anneals to M13 (+)-strand DNA.

<400> SEQUENCE: 3
tttttttttt tttttaccac acccgccgcg cttaatgcgc cgctacaggg cgcgtactat     60
ggttgctttg acgag                                                      75

<210> SEQ ID NO 4
<211> LENGTH: 40
<212> TYPE: DNA
<213> ORGANISM: Artificial Sequence
<220> FEATURE:

-continued

```
<223> OTHER INFORMATION: Description of Artificial Sequence:
      Oligonucleotide primer that anneals to M13 (+)-strand DNA.

<400> SEQUENCE: 4
tttttttttt tcctcaagag aaggattagg attagcgggg                              40

<210> SEQ ID NO 5
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide primer that anneals to M13 (+)-strand DNA.

<400> SEQUENCE: 5
tttttttttt acaaagggc gacattcaac cgattgaggg                               40

<210> SEQ ID NO 6
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide primer that anneals to M13 (+)-strand DNA.

<400> SEQUENCE: 6
tttttttttt cctgaacaaa gtcagagggt aattgagcgc                              40

<210> SEQ ID NO 7
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide primer that anneals to M13 (+)-strand DNA.

<400> SEQUENCE: 7
tttttttttt acaacatgtt cagctaatgc agaacgcgcc                              40

<210> SEQ ID NO 8
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide primer that anneals to M13 (+)-strand DNA.

<400> SEQUENCE: 8
tttttttttt catcgggaga aacaataacg gattcgcctg                              40

<210> SEQ ID NO 9
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide primer that anneals to M13 (+)-strand DNA.

<400> SEQUENCE: 9
tttttttttt atgcgcgaac tgatagccct aaaacatcgc                              40
```